US012700500B2

(12) United States Patent
Lee et al.

(10) Patent No.: US 12,700,500 B2
(45) Date of Patent: Aug. 4, 2026

(54) METHODS, SYSTEMS, AND COMPUTER READABLE MEDIA FOR MANAGING MEDICAL DEVICES

(71) Applicant: The Trustees of the University of Pennsylvania, Philadelphia, PA (US)

(72) Inventors: Insup Lee, Newtown Square, PA (US); Hyonyoung Choi, Philadelphia, PA (US); Amanda Lor, Somerville, MA (US); Michael Megonegal, Philadelphia, PA (US); Xiayan Ji, Philadelphia, PA (US); Amanda Watson, Brigantine, NJ (US); Jean Park, Philadelphia, PA (US); Oleg Sokolsky, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 21 days.

(21) Appl. No.: 18/542,492

(22) Filed: Dec. 15, 2023

(65) Prior Publication Data

US 2024/0339206 A1 Oct. 10, 2024

Related U.S. Application Data

(60) Provisional application No. 63/432,969, filed on Dec. 15, 2022.

(51) Int. Cl.
*G16H 40/40* (2018.01)
*G16H 10/60* (2018.01)
*G16H 40/67* (2018.01)

(52) U.S. Cl.
CPC ............. *G16H 40/40* (2018.01); *G16H 10/60* (2018.01); *G16H 40/67* (2018.01)

(58) Field of Classification Search
CPC ........ G16H 40/40; G16H 10/60; G16H 40/67; G16H 40/20; G16H 20/40
See application file for complete search history.

(56) References Cited

U.S. PATENT DOCUMENTS

| | | | | |
|---|---|---|---|---|
| 2007/0257788 | A1* | 11/2007 | Carlson | A61B 5/0002 |
| | | | | 600/300 |
| 2020/0282163 | A1* | 9/2020 | Schranz | A61M 16/024 |
| 2024/0115202 | A1* | 4/2024 | Tran | A61B 5/0022 |

OTHER PUBLICATIONS

Medtech and the internet of medical things, https://www2.deloitte.com/uk/en/pages/life-sciences-andhealthcare/articles/medtech-and-the-internet-of-medical-things.html, accessed: Jun. 2021.

(Continued)

*Primary Examiner* — Chinyere Mpamugo
(74) *Attorney, Agent, or Firm* — Jenkins, Taylor & Hunt, P.A.

(57) ABSTRACT

A system for managing a plurality of medical devices includes a stream processor for receiving medical data from a plurality of medical devices and for generating metadata and storing the medical data and the metadata for each of the devices. The system further includes data storage for storing the medical data and the metadata. The system further includes a communications interface for implementing at least one communications protocol for providing access to the medical data and the metadata. The system further includes an application for accessing the medical data and the metadata via the communications interface and generating, based on the medical data and the metadata, output indicative of operating status of the medical devices.

27 Claims, 16 Drawing Sheets

(56) References Cited

OTHER PUBLICATIONS

"Projected size of the internet of things (iot) in healthcare market worldwide from 2016 to 2025," https://www.statista.com/statistics/997959/worldwide-internet-ofthings-in-healthcare-market-size/, published: Dec. 2016.

R. L. Read, L. Clarke, and G. Mulligan, "Ventmon: An open source inline ventilator tester and monitor," HardwareX, vol. 9, p. e00195, 2021.

H. Nguyen, R. Ivanov, S. B. DeMauro, and J. Weimer, "Repulmo: A remote pulmonary monitoring system," SIGBED Rev., vol. 16, No. 2, p. 46-50, Aug. 2019. [Online]. Available: https://doi.org/10.1145/3357495.3357501.

M. Kasparick, M. Schmitz, B. Andersen, M. Rockstroh, S. Franke, S. Schlichting, F. Golatowski, and D. Timmermann, "Or. net: a service oriented architecture for safe and dynamic medical device interoperability," Biomedical Engineering/Biomedizinische Technik. vol. 63, No. 1, pp. 11-30. 2018.

B. Almadani, M. Bin-Yahya, and E. M. Shakshuki, "E-ambulance: realtime integration platform for heterogeneous medical telemetry system," Procedia Computer Science, vol. 63, pp. 400-407, 2015.

M. V. Perez, K. W. Mahaffey. H. Hedlin, J. S. Rumsfeld, A. Garcia, T. Ferris, V. Balasubramanian, A. M. Russo, A. Rajmane, L. Cheung et al., "Large-scale assessment of a smartwatch to identify atrial fibrillation," New England Journal of Medicine, vol. 381, No. 20, pp. 1909-1917. 2019.

A. Prudenzi, A. Fioravanti, and M. Regoli, "A low-cost internet of things integration platform for a centralized supervising system of building technology systems in hospitals," in 2018 IEEE International Conference on Environment and Electrical Engineering and 2018 IEEE Industrial and Commercial Power Systems Europe.

D. Arney, J. Plourde, and J. M. Goldman, "Openice medical device interoperability platform overview and requirement analysis," Biomedical Engineering/Biomedizinische Technik, vol. 63, No. 1, pp. 39-47, 2018.

R. Ivanov, H. Nguyen, J. Weimer, O. Sokolsky, and I. Lee, "Openicelite: Towards a connectivity platform for the internet of medical things," in 2018 IEEE 21st International Symposium on Real-Time Distributed Computing (ISORO). IEEE, 2018, pp. 103-106.

J. Woodbridge, H. Noshadi, A. Nahapetian, and M. Sarrafzadeh, "Hip: Health integration platform," in 2010 8th IEEE International Conference on Pervasive Computing and Communications Workshops (PERCOM Workshops), 2010, pp. 340-345.

Z. Yang, Q. Zhou, L. Lel, K. Zheng, and W. Xiang, "An lot-cloud based wearable ecg monitoring system for smart healthcare," Journal of medical systems, vol. 40, No. 12, pp. 1-11, 2016.

H. Xia, I. Asif, and X. Zhao, "Cloud-ecg for real time ecg monitoring and analysis," Computer methods and programs in biomedicine, vol. 110, No. 3, pp. 253-259, 2013.

Z. A. Al-Odat, S. K. Srinivasan, E. Al-qtiemat, M. A. L. Dubasi, and S. Shuja, "Iot-based secure embedded scheme for insulin pump data acquisition and monitoring," arXiv preprint arXiv:1812.02357, 2018.

P. Asare, D. Cong, S. G. Vattam, B. Kim, A. King, O. Sokolsky, I. Lee, S. Lin, and M. Mullen-Fortino, "The medical device dongle: An open-source standards-based platform for interoperable medical device connectivity," in Proceedings of the 2nd ACM SIGHIT International Health Informatics Symposium 2012 on 667-672.

"Neuron, medical device integration, capsule technologies," https://capsuletech.com/neuron, accessed: Jun. 2021.

"Keras documentation: Timeseries anomaly detection using an autoencoder," https://keras.io/examples/timeseries/timeseries anomaly detection/. May 31, 2020.

B. Scholkopf, R. C. Williamson, A. J. Smola, J. Shawe-Taylor, J. C. Platt et al., "Support vector method for novelty detection." in NIPS, vol. 12. Citeseer, 1999, pp. 582-588.

Moloud Abdar, Farhad Pourpanah, Sadiq Hussain, Dana Rezazadegan, Li Liu, Mohammad Ghavamzadeh, Paul Fieguth, Xiaochun Cao, Abbas Khosravi, U Rajendra Acharya, et al. 2021. A review of uncertainty quantification in deep learning: Techniques, applications and challenges, Information Fusion 76 (2021). 243-297.

Fadi Al-Turiman, Muhammad Hassan Nawaz, and Umit Deniz Ulusar. 2020. Intelligence in the Internet of Medical Things era: A systematic review of current and future trends. Computer Communications 150 (2020), 644-660.

Parisa Alaei and Fakhroddin Noorbehbahanl. 2017. Incremental anomaly-based intrusion detection system using limited labeled data. In 2017 3th International Conference on Web Research (ICWR). IEEE, 178-184.

Merve Astekin, Selim Özcan, and Hasan Sözer. 2019. Incremental analysis of large-scale system logs for anomaly detection. In 2019 IEEE International Conference on Big Data (Big Data). IEEE, 2119-2127.

Monowar H Bhuyan, Dhruba K Bhattacharyya, and Jugal K Kalita. 2012. Survey on incremental approaches for network anomaly detection. arXiv preprint arXiv:1211.4493 (2012).

Elnaz Bigdell, Mahdi Mohammadi, Bijan Raahemi, and Stan Matwin. 2018. Incremental anomaly detection using two-layer cluster-based structure. Information Sciences 429 (2018), 315-331.

Milad Chenaghlou, Masud Moshtaghi, Christopher Leckie, and Mahsa Salehi. 2018. Online clustering for evolving data streams with online anomaly detection. In Pacific-Asia Conference on Knowledge Discovery and Data Mining. Springer 508-521.

Hyonyoung Choi, Amanda Lor, Mike Megonegal, Xiayan Ji, Amanda Watson, James Weimer, and Insup Lee. 2021. VitalCore: Analytics and Support Dashboard for Medical Device Integration. In 2021 IEEE/ACM Conference on Connected Health: Applications, Systems and Engineering Technologies (CHASE) 82-86.

Raj Deshmukh and Inseok Hwang. 2019. Incremental-learning-based unsupervised anomaly detection algorithm for terminal airspace operations. Journal of Aerospace Information Systems 16, 9 (2019), 362-384.

Arthur Gatouillat, Youakim Badr, Bertrand Massot, and Ervin Sejdić. 2018. Internet of medical things: A review of recent contributions dealing with cyber-physical systems in medicine. IEEE internet of things journal 5, 5 (2018), 3810-3822.

Nico Görnitz, Marius Kloft, Konrad Rieck, and Ulf Brefeld. 2013. Toward supervised anomaly detection. Journal of Artificial Intelligence Research 46 (2013), 235-262.

John C Knight. 2002. Safety critical systems: challenges and directions. In Proceedings of the 24th international conference on software engineering. 547-550.

Aleksandar Lazarevic, Levent Ertoz, Vipin Kumar, Aysel Ozgur, and Jaideep Srivastava. 2003. A comparative study of anomaly detection schemes in network intrusion detection. In Proceedings of the 2003 SIAM international conference on data mining. SIAM. 25-36.

Insup Lee and Oleg Sokolsky. 2010. Medical cyber physical systems. In Design automation conference. IEEE, 743-748.

Shuo Li, Xiayan Ji, Edgar Dobriban, Oleg Sokolsky, and Insup Lee. 2022. PAC-Wrap: Semi-Supervised PAC Anomaly Detection. https://doi.org/10.48550/ARXIV.2205.10798.

Yongxin Liu, Jian Wang, Jiangiang Li, Shuteng Niu, and Houbing Song. 2021. Class-incremental learning for wireless device identification in IoT. IEEE Internet of Things Journal 8, 23 (2021), 17227-17235.

Guansong Pang, Chunhua Shen, and Anton van den Hengel. 2019. Deep anomaly detection with deviation networks. In Proceedings of the 25th ACM SIGKDD international conference on knowledge discovery & data mining. 353-362.

Harris Papadopoulos, Kostas Proedrou, Volodya Vovk, and Alex Gammerman, 2002. Inductive confidence machines for regression. In European Conference on Machine Learning. Springer, 345-356.

Sangdon Park, Osbert Bastani, Nikolai Matni, and Insup Lee. 2020. PAC confidence sets for deep neural networks via calibrated prediction. International Conference on Learning Representations (ICLR) (2020).

Sangdon Park, Edgar Dobriban, Insup Lee, and Osbert Bastani. 2022. Pac prediction sets under covariate shift. International Conference on Learning Representations (ICLR) (2022).

Adam Paszke, Sam Gross, Francisco Massa, Adam Lerer, James Bradbury, Gregory Chanan, Trevor Killeen, Zeming Lin, Natalia

(56)          References Cited

OTHER PUBLICATIONS

Gimelshein, Luca Antiga, et al. 2019. Pytorch: An imperative style, high-performance deep learning library. Advances in neural information processing systems 32 (2019).

Kirthanaa Raghuraman, Monisha Senthurpandian, Monisha Shanmugasundaram, V Vaidehi, et al. 2014. Online incremental learning algorithm for anomaly detection and prediction in health care.

Lukas Ruff, Robert A Vandermeulen, Nico Görnitz, Alexander Binder, Emmanuel Müller, Klaus-Robert Müller, and Marius Kloft. 2020. Deep semi-supervised anomaly detection. International Conference on Learning Representations (ICLR) (2020).

Kenneth Joseph Ryan and Mark Vere Culp. 2015. On semi-supervised linear regression in covariate shift problems. The Journal of Machine Learning Research 16, 1 (2015), 3183-3217.

Mahsa Salehi and Lida Rashidi. 2018. A Survey on Anomaly detection in Evolving Data: [with Application to Forest Fire Risk Prediction]. ACM SIGKDD Explorations Newsletter 20, 1 (2018), 13-23.

Steffen Schneider, Evgenia Rusak, Luisa Eck, Oliver Bringmann, Wieland Brendel, and Matthias Bethge. 2020. Improving robustness against common corruptions by covariate shift adaptation. Advances in Neural Information Processing Systems 33 (2020). 11539-11551.

Bernhard Schölkopf, Robert C Williamson, Alex Smola, John Shawe-Taylor, and John Platt. 1999. Support vector method for novelty detection. Advances in neural information processing systems 12 (1999).

Sue Sendelbach and Marjorie Funk. 2013. Alarm fatigue: a patient safety concern. AACN advanced critical care 24, 4 (2013), 378-386.

Yang Shi, Maoran Xu, Rongwen Zhao, Hao Fu, Tongshuang Wu, and Nan Cao. 2019. Interactive Context-Aware Anomaly Detection Guided by User Feedback. IEEE Transactions on Human-Machine Systems 49, 6 (2019), 550-559. https://doi.org/10.1109/THMS.2019.2925195.

Hongchao Song, Zhuging Jiang, Aidong Men, and Bo Yang. 2017. A hybrid semi-supervised anomaly detection model for high-dimensional data. Computational intelligence and neuroscience 2017 (2017).

Masashi Sugiyama, Matthias Krauledat, and Klaus-Robert Müller. 2007. Covariate shift adaptation by importance weighted cross validation. Journal of Machine Learning Research 8, 5 (2007).

Masashi Sugiyama, Taiji Suzuki, Shinichi Nakajima, Hisashi Kashima, Paul von Bünau, and Motoaki Kawanabe 2008. Direct importance estimation for covariate shift adaptation. Annals of the Institute of Statistical Mathematics 60, 4 (2008) 699-746.

Swee Chuan Tan, Kai Ming Ting, and Tony Fei Liu. 2011. Fast anomaly detection for streaming data. In Twenty-second international joint conference on artificial intelligence.

Liang Tang, Tao Li, Florian Pinel, Larisa Shwartz, and Genady Grabarnik. 2012. Optimizing system monitoring configurations for non-actionable alerts. In 2012 IEEE Network Operations and Management Symposium. IEEE, 34-42.

Vincent Vercruyssen, Wannes Meert, Gust Verbruggen, Koen Maes, Ruben Bäumer, and Jesse Davis. 2018 Semi-Supervised Anomaly Detection with an Application to Water Analytics. In 2018 IEEE International Conference on Data Mining (ICDM). 527-536. https://doi.org/10.1109/ICDM.2018.00068.

Vladimir Vovk. 2012. Conditional validity of inductive conformal predictors. In Asian conference on machine learning. PMLR, 475-490.

Vladimir Vovk, Alex Gammerman, and Glenn Shafer. 2005. Algorithmic learning in a random world. Springer Science & Business Media.

Markus Wurzenberger, Florian Skopik, Max Landauer, Philipp Greitbauer, Roman Fiedler, and Wolfgang Kastner. 2017. Incremental clustering for semi-supervised anomaly detection applied on log data. In Proceedings of the 12th International Conference on Availability, Reliability and Security. 1-6.

Weizun Zhao, Lishuai Li, Sameer Alam, and Yanjun Wang. 2021. An incremental clustering method for anomaly detection in flight data. Transportation Research Part C: Emerging Technologies 132 (2021), 103406.

Aurick Zhou and Sergey Levine. 2021. Training on Test Data with Bayesian Adaptation for Covariate Shift. Advances in Neural Information Processing Systems 34 (2021).

* cited by examiner

RECEIVE MEDICAL DATA FROM MEDICAL DEVICES, GENERATE METADATA, AND STORE MEDICAL DATA AND METADATA    600

PROVIDE COMMUNICATIONS INTERFACE FOR ACCESSING MEDICAL DATA AND METADATA    602

PROVIDE APPLICATION FOR ACCESSING MEDICAL AND METADATA VIA COMMUNICATIONS INTERFACE AND GENERATE OUTPUT INDICATIVE OF MEDICAL DEVICE OPERATING STATUS    604

(a) t=100

(b) t=1000

(c) t=5000

(a) PRAUC on synthetic data.

(b) ROCAUC on synthetic data.

(c) PRAUC on VitalCore data.

(d) ROCAUC on VitalCore data.

METHODS, SYSTEMS, AND COMPUTER READABLE MEDIA FOR MANAGING MEDICAL DEVICES

PRIORITY CLAIM

This application claims priority to U.S. Provisional Patent Application Ser. No. 63/432,969 filed Dec. 15, 2022, the disclosure of which is incorporated herein by reference in its entirety.

GOVERNMENT INTEREST

This invention was made with government support under EB029767 awarded by the National Institutes of Health, 1915398 and 2125561 awarded by the National Science Foundation, and W911NF-20-1-0080 awarded by the Army Research Office. The government has certain rights in the invention.

TECHNICAL FIELD

The subject matter described herein relates to managing medical groups of medical devices, including medical devices from different vendors. More particularly, the subject matter described herein relates to a system called VitalCore, which provides a dashboard for managing groups of medical devices. The subject matter described herein also includes applications for monitoring medical device operational status, generating ventilation alerts for new intubations detected from HL7 data, and generating alerts for anomalies detected from HL7 data.

BACKGROUND

Medical professionals spend extensive time collecting, validating, reviewing, and analyzing medical device data. These devices use vendor-specific applications with lengthy troubleshooting times, causing extended downtimes where medical professionals have to manually document patient data in the electronic health record (EHR). Manual logging of this data creates delays and leaves it vulnerable to errors, manipulation, and omissions.

Accordingly, there exists a need for improved methods, systems, and computer readable media for managing medical devices that avoid at least some of these difficulties.

SUMMARY

The subject matter described herein includes a medical device integration platform, referred to as VitalCore, that supports access to medical device data in real-time. VitalCore includes three applications, Medical Device Dashboard, Ventilation Alert, and Anomaly Detector. In the Medical Device Dashboard, we reduced, by up to six times, the amount of time required of medical professionals, clinical engineers, and IT analysts by simplifying the troubleshooting workflow, thus decreasing downtimes and increasing clinical productivity. In Ventilation Alert, we demonstrated the ability to assist medical professionals by alerting them to newly ventilated patients. In Anomaly Detector, we showed that we could predict anomalous patterns in our data with 93% accuracy.

A system for managing a plurality of medical devices includes a stream processor for receiving medical data from a plurality of medical devices and for generating metadata and storing the medical data and the metadata for each of the devices. The system further includes data storage for storing the medical data and the metadata. The system further includes a communications interface for implementing at least one communications protocol for providing access to the medical data and the metadata. The system further includes an application for accessing the medical data and the metadata via the communications interface and generating, based on the medical data and the metadata, output indicative of operating status of the medical devices.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Exemplary implementations of the subject matter described herein will now be explained with reference to the accompanying drawings, of which:

FIG. 3A illustrates the home screen of the dashboard application, and FIG. 3B illustrates a display of HL7 messages by the application;

FIG. 13A illustrates that with a single anomaly calibration set, the normal calibration set is contaminated by anomalies that are perceived as normal. Hence it has two discrete anomaly score distributions. FIG. 13B illustrates that with the fine-grained calibration sets, we can distinguish normal and anomalous distributions;

In FIG. 14A, the normal calibration set is mixed with perceived normal anomalies with a single anomaly calibration set, leading to a confounding anomaly score distribution. FIG. 14B illustrates that with the fine-grained calibration sets, we can distinguish normal and anomalous distributions;

FIG. 16 illustrates that as $\epsilon$ and $\delta$ grow, the uncertain region shrinks.

DETAILED DESCRIPTION

Figure 1:
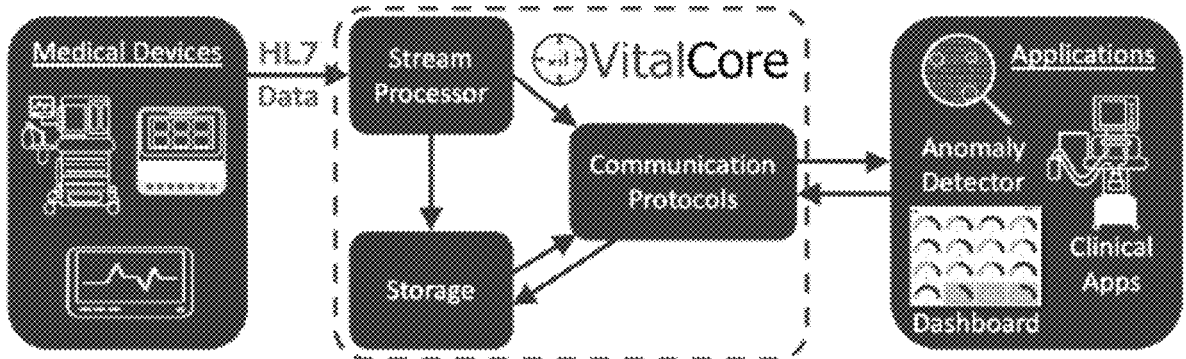
FIG. 1 is a block diagram illustrating an exemplary VitalCore system architecture.
Figure 2:
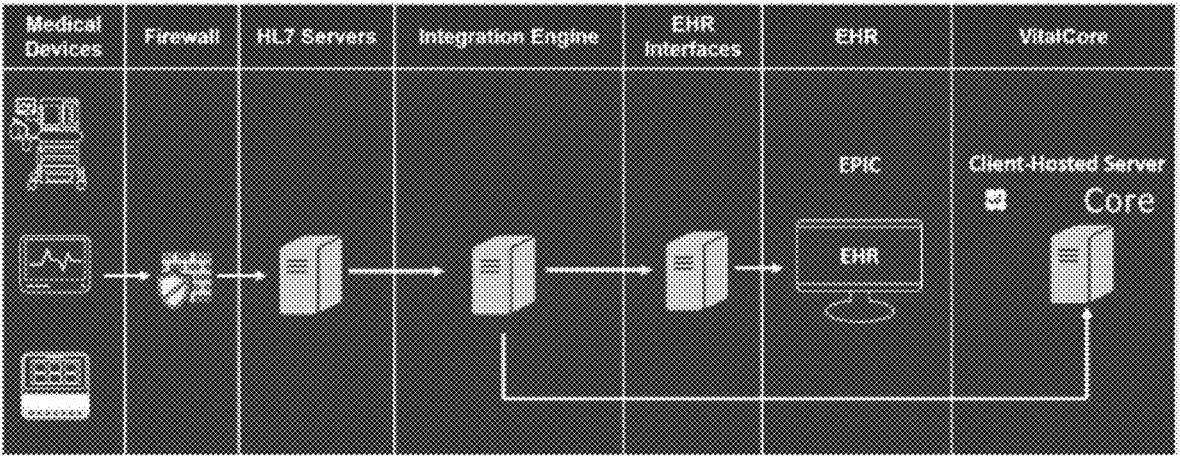
FIG. 2 is a block diagram illustrating integration of VitalCore into a medical information system, such as a hospital integration system.

The Internet of Medical Things (IoMT) is a complex system of networked medical devices that share medical device data with healthcare professionals to enable new and innovative medical services. These devices range from wearables (e.g., Fitbit) to implantables (e.g., pacemakers) and medical equipment (e.g., magnetic resonance imaging (MRI) machines and ventilators). It is even expected that upwards of 68% of all medical devices manufactured will be connected by 2022 [1]. Further, IoMT is expected to continue growing as forecasts predict it will reach a market value of over $135 billion by 2025 [2]. As the IoMT market continues to grow, the systems that support these devices will need to adapt, bringing new software, hardware, and cybersecurity solutions.

As medical devices come online, systems are developed to support the storage, transmission, and security of medical device data. This has led to non-standardized vendor-specific applications that require specialized training. Thus, medical professionals spend excessive time interfacing with medical devices to collect, validate, review, and analyze medical device data. When these devices malfunction, not only are there extended downtimes for the device, medical professionals are required to manually document device data in the electronic health record (EHR), distracting them from direct patient care. Consequently, manual logging of this data leaves it vulnerable to errors, manipulation, and omissions.

The integration of medical equipment in the IoMT has led to massive improvement in the quality of patient care [3]-[7]. It has also led to the coordination of Medical Cyber-Physical System (MCPS) and IoMT to provide better information to the caregiver, detect failures of individual devices, and improve patient safety and treatment effectiveness. Thus, researchers have started developing integration platforms that allow for a large number of medical devices. These platforms focus on bringing old hardware online [8] and interoperability between devices [9]-[11]. VitalCore outperforms these software platforms by ensuring clinical devices are operational while providing a user-friendly dashboard for caregivers without technical backgrounds. Its dashboard is designed with troubleshooting in mind to minimize downtimes creating a more efficient workflow in medical environments.

Currently, Penn Medicine has over 3,000 integrated medical devices over thirteen facilities from seven different vendor networks. Consequently, this extensive network of medical devices has led to the many challenges discussed previously. To address these challenges, we developed Vital-Core, a platform to manage clinical devices and proactively keep them operable while improving the workflow for the IT analysts and clinical engineers. VitalCore not only has clinical benefits but technical and research benefits as well. Clinically, manual documentation is reduced, providing time savings and real-time, accurate data is fed to clinical decision support systems. To demonstrate this, we built three applications Medical Device Dashboard, Ventilation Alert, and Anomaly Detector. Technically, troubleshooting efficiency is increased to minimize downtime, and responses are moved from reactive to proactive. This efficiency has led to a decrease of three to six times the time needed for troubleshooting. Additionally, data is archived to support future research and analysis. Specifically, our contributions are:

1) Development of VitalCore, a vendor-neutral platform that, to our knowledge, is the first of its kind in the industry that manages clinical devices and proactively keeps them operable while improving the workflow for IT analysts and clinical engineers.

2) The VitalCore system architecture supports the development and deployment of various applications, including user-friendly dashboards, clinical alert systems, and anomaly detection.

The remainder of this document is structured as follows: First, we summarized the work related to this paper in Section II. In Section III, we describe the VitalCore system. Then, Section IV describes applications in which VitalCore is being used. In Section V, we evaluate our system. Finally, we conclude in Section VI.

II. RELATED WORK

The tendency of migrating medical devices online has become more and more prominent in the world of the Internet of Medical Things. Devices such as ventilators [3], pulmonary monitors [4], medical equipment in ambulances [6], and surgical devices in operating rooms [5] are being brought online. Additionally, integrating devices with an online platform has made remote health monitoring more convenient. Devices such as ECGs [12], [13], insulin pumps [14], and heart rate monitoring via Apple Watches [7] track a patient's health in the comfort of their own home and send this data back to clinicians for further analysis. As IoMT brings these monitoring devices online, the resulting Medical Cyber-Physical System (MCPS) has the ability to provide more intelligent information to clinicians and caregivers, detect failures of devices, and improve patient safety and treatment effectiveness.

Researchers and engineers have begun developing integrated systems that manage a large number of heterogeneous medical devices spanning the domains of hardware and software. For instance, Prudenzi et al. [8] implemented a hardware system that installed a Raspberry Pi 3 near medical devices of interest and connected them to an online supervisory system. As are et al. provides a dongle to connect previously unconnected medical devices [15]. In addition, software frameworks tackle the interoperability challenges between devices. OpenICE [9] is an open-source Integrated Clinical Environment (ICE) that assists in research for connecting IoMT devices. Expanding on that, OpenICE-lite provides security guarantees and real-time data visualization and analysis. HIP is an end-to end software integration platform that generalized the wireless body sensor frame-work to test for correctness and performance in health applications. VitalCore outperforms other software plat-forms because it not only maintains clinical devices and ensures that they are operational but also provides a user friendly GUI dashboard for caregivers without technical backgrounds. This is a critical functionality to maintain efficient workflows in medical environments where users may not be technology experts.

III. VITALCORE SYSTEM

The overall architecture of VitalCore is depicted in FIG. 1. VitalCore takes as input the HL7 data feed streaming from medical devices. This data is fed into the stream processor for processing and routing. Then, data is stored to be displayed in the dashboard and for future analysis. Next, the communication protocols provide the processed data to the applications. Applications can send additional data back to VitalCore, in which the communication protocols can route this data to our storage.

a. HL7 Data: Health Level Seven, commonly known as HL7, is a set of widely supported international standards that promote the transfer of medical data between software applications used by various healthcare providers. By providing commonly supported data transfer guidelines, medical data can be exchanged across EHRs and other software applications without ambiguity and risk of misinterpretation. In our test environment, we received the HL7 Data stream not directly from the medical devices but from the integrated middleware system. However, VitalCore supports any medical devices that are capable of networking or support a network integration adapter (e.g., Capsule Neuron [16]).

b. Stream Processor: The Stream Processor accomplishes two tasks: it generates and updates meta-data and routes the data to storage and the communication protocols. To generate metadata, we extract the device identifier and the arrival time of the message to Vital-Core. With this information, we generate two meta-data tables: the timestamp history for each device and the latest timestamp for each device. Then, the data and meta-data are sent to storage and the applications.

c. Storage: VitalCore uses TimescaleDB for HL7 Data and MongoDB for any other data. HL7 data is time-series as each medical device is sending its HL7 data repeatedly over time. Hence, there are performance and scalability benefits to storing HL7 data in a time-series database. MongoDB stores our non-time-series data such as user accounts, metadata, application-specific data, etc. While these databases are separate, we use common identifiers to provide connections between the data.

d. Communication Protocols: Communication Protocols include REST-API (REpresentational State Transfer API) and Web-Socket. REST-API uses queries to access data from storage. But, some of the applications need a real-time stream of HL7 data. In this case, HL7 Stream Processor forwards the HL7 data directly to the applications via a Web-Socket. The streaming data is directly sent from the HL7 Stream Processor bypassing the database. This data can also be sent back from the applications to the communication protocols for further routing to storage or other applications.

e. Applications: In VitalCore, we prioritized flexibility and modularity to promote the support and creation of many applications. Thus, applications with varied func-tionalities can be built on top of the VitalCore system. This allows for custom, tailored applications that meet the specific needs of clinicians and IT staff to be built. In this paper, we will discuss the following scenarios: medical device dashboard, ventilation alert, and anomaly detection. Detailed functionalities of the applications will be explained in Section IV.

IV. APPLICATIONS

VitalCore is used in three applications: Medical Device Dashboard, Ventilation Alert, and Anomaly Detector. The Medical Device Dashboard provides clinicians access to real-time, accurate data in the EHR with a user-friendly GUI. Further, it streamlines the troubleshooting process for IT staff. Ventilation alert showcases the integration of medi-cal devices, in this case, ventilators, to send data in real-time to the EHR and generates alerts sent to medical profession-als. The anomaly detector detects anomalies in the usage patterns of medical devices and groupings of medical devices.

A. Medical Device Dashboard

Figure 3A:
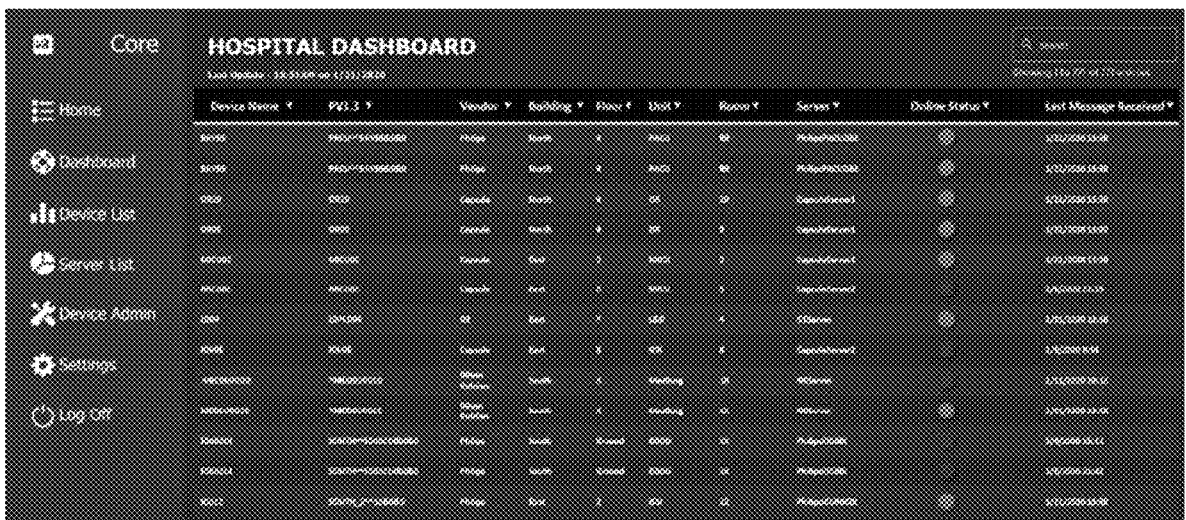
FIGS. 3A and 3B illustrate computer screen shots displayed by a medical device dashboard application.
Figure 3B:
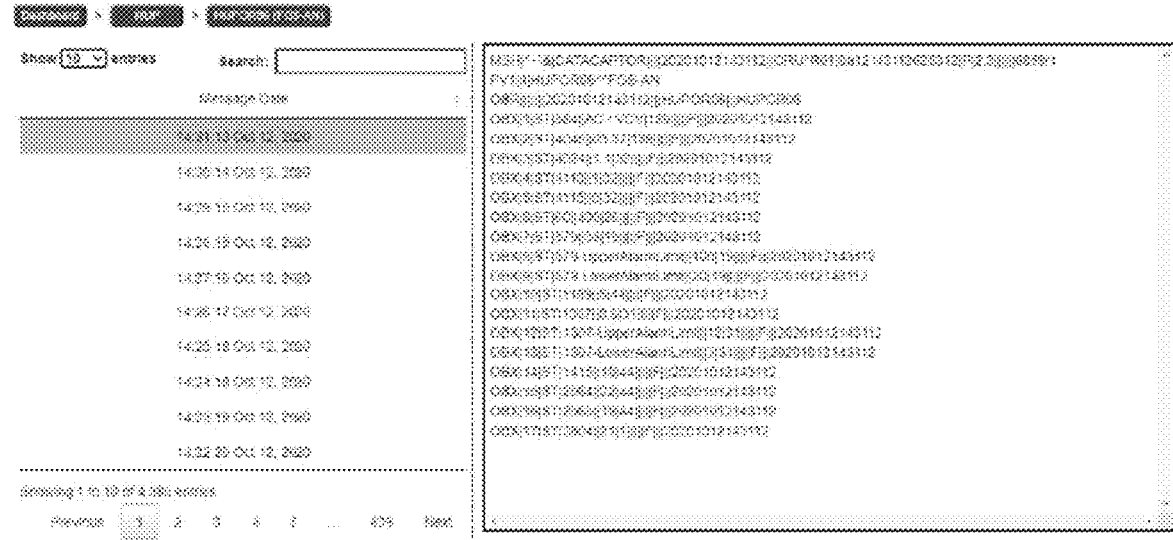

The medical device dashboard shown in FIGS. 3A and 3B is a graphical user interface (GUI) designed to allow users (e.g., IT analysts and clinical engineers) to find and identify essential information (e.g., device name, location, vendor, etc.) within the timespan of a minute. To tailor the dashboard to those using it, we analyzed the usage patterns of our users to identify important functionalities that support the navi-gation of existing tools. After discovering the most valuable features, we created a mock-up user interface (UI) which was employed to collect user feedback. From this feedback, we redesigned our UI and tested it with real-time data.

Figure 4:
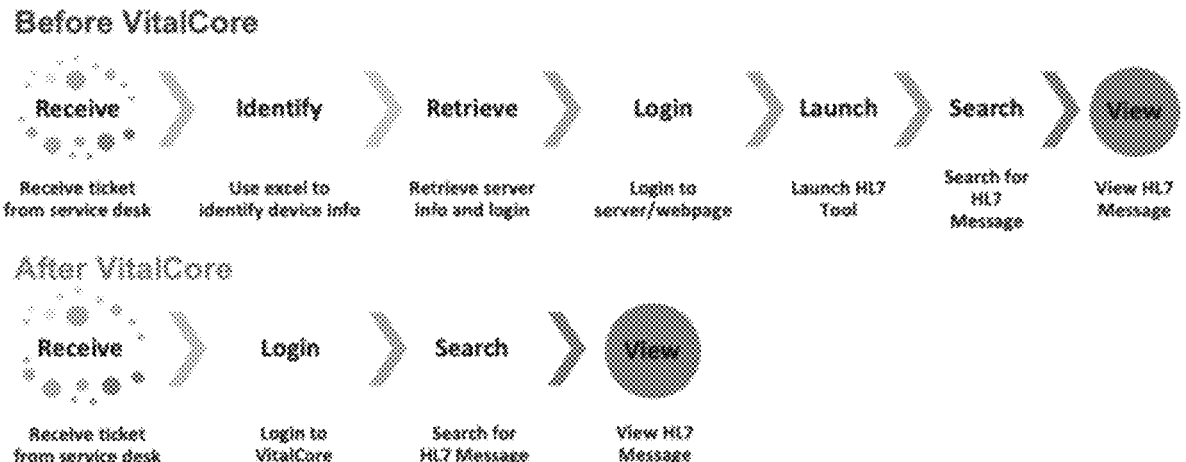
FIG. 4 is a work flow diagram illustrating exemplary work flows for troubleshooting a medical device with and without VitalCore.

1. First, we observed the troubleshooting workflow of the IT analysts with the goal of saving their time by improving the workflow with an integrated approach to medical device management. We found that when a device needed troubleshooting, the IT analysts, in gen-eral, performed the seven steps shown in FIG. 4. Among these steps, we identified where improvements could be made. Three steps were deemed unnecessary and time-consuming. We determined that they could be accounted for in a single login to the VitalCore system: identifying device info, retrieving server information, and launching HL7 tests. This reduced our trouble-shooting workflow to four steps, as shown in FIG. 4. VitalCore reduced the need for analysts to use an excel spreadsheet, look for login credentials and server names, run lengthy searches, or contact other teams for support. Further, analysts were limited in the past by relying on vendor solutions and tools that were specific to each vendor's medical technology. For example, one vendor's app displayed the HL7 data output status for their technology, while other vendors did not. VitalCore reduced the need to learn to use multiple solutions and provides a single, standardized platform for our users.

B. Ventilation Alert

Respiratory Therapists (RT) in the ICU manage patients on ventilators based on clinician-developed treatment plans. A large portion of their job revolves around monitoring these patients to evaluate their treatment. When a patient is not reacting as expected, the RT troubleshoots the issue and consults with clinicians to make changes to the ventilator settings. To free up the RT to focus on the more critical, troubleshooting portion of their job, a telemedicine respiratory therapist (eRT) is stationed at the virtual intensive care unit (VICU) to remotely monitor newly intubated patients. When a patient is not reacting well to treatment, the eRT contacts the RT for troubleshooting.

Currently, ventilators do not send a start status message to the EHR, and thus the eRT is not notified through the VICU. The eRT relies on calls from the onsite nurse or respiratory therapist (RT) or validated data in the EHR, which is not real-time. As a result, patient monitoring via the VICU is delayed. To solve this problem, ventilation start time can be extracted from the real-time HL7 messages sent every minute from the ventilators. Within these messages, a variable ID, expired tidal volume (TV), can be used as an indicator that a patient has been intubated. Expired TV is the volume of air that a patient breathes out. If an expired TV has a value greater than zero, the receive time for the message is noted as the ventilation start time. To alert the eRT, an intubation alert is sent as a text message to the eRTs phone.

When only using the expired Tidal Volume to determine start time, we noticed many false positives, largely with patients who were already ventilated. To minimize these false positives, the following logic was implemented:
1. If the patient-name is different from the other devices, update the patient-name and always send an alert
2. If the patient-name is the same as the other devices and the previous stop time is less than an hour, skip the alert.
3. Otherwise, send an alert. The alert system is currently under evaluation for its effectiveness and safety.

C. Anomaly Detector

An important factor in changing reactive troubleshooting to proactive is monitoring anomalies in the usage pattern of medical devices. For example, a medical device sends a message every minute during business hours but sends a reduced number of messages after business hours and during weekends. But when unexpected events occur, such as an emergency for a patient or a network outage, we should detect and respond appropriately to the event. VitalCore detects these anomalous situations in real-time to bring nursing or IT personnel to investigate them. Moreover, some anomalies appear in several devices within the same group (e.g., room, floor, nursing units). VitalCore detects these patterns as well, allowing for a more comprehensive view of the anomalies.

We train machine learning models to learn the normal usage patterns of devices. We monitor the usage patterns of 60-second intervals, weekday, and weekend, where each pattern has its own model. The trained models retain a compressed representation of the patterns and use it to reconstruct the input. After that, we compute the Mean Absolute Error (MAE) between the reconstructed input and the raw input. Then, during training, we fed all training instances to the model and chose the maximum reconstruction error as the threshold T to determine anomalies. During testing, each new instance i received in real-time is fed to the trained models where the maximum reconstruction error $err_i$ among all pattern models is calculated. If $err_i > T$, we declare anomaly. Otherwise, we consider it normal. An incremental anomaly detector that adapts to shifts in anomaly data distributions will be described in detail below.

V. EVALUATION

We evaluate our system in each of the applications described in the previous section. First, we consider the impact the Medical Device Dashboard has on the troubleshooting workflow. Second, we assess the ventilator alert system. Finally, we analyze the anomaly detector.

A. Medical Device Dashboard

Figure 5:
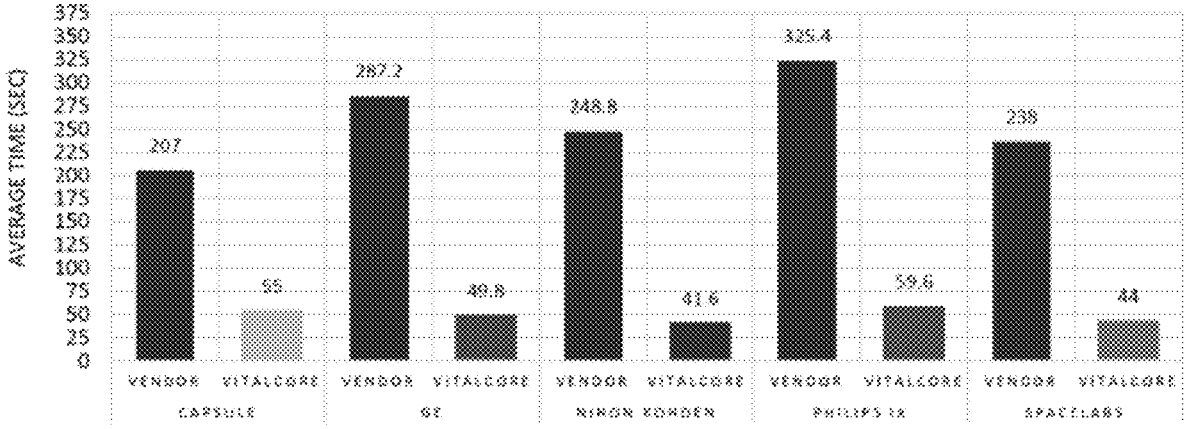
FIG. 5 is a histogram comparing medical device troubleshooting times with and without VitalCore.

A goal of VitalCore is to increase troubleshooting efficiency to minimize downtimes. To do this, we simplified the troubleshooting workflow as shown in FIG. 4. We evaluate the improved workflow by comparing the time it takes to troubleshoot using VitalCore to using vendor-specific software. FIG. 5 shows a direct comparison between multiple vendors and VitalCore. Overall, we see a decrease of three to six times the amount of time (4.5 minutes to 50 seconds) needed to troubleshoot for these vendors exemplifying the benefits of using VitalCore during the troubleshooting process.

B. Ventilation Alert

With device integration, respiratory therapists spend five minutes per ventilator check to validate ventilator data in the EHR. When there is a disruption in the HL7 data flow from the ventilator to the EHR, respiratory therapists must manually document readings and settings, which takes three times longer (15 minutes) per ventilator check. The longer it takes for analysts to troubleshoot and restore data flow, the more time respiratory therapists must spend on manual documentation instead of directly caring for their patients.

We conducted a pilot study using 139 ventilators where a telemedicine respiratory therapist (eRT) is stationed at the virtual intensive care unit (VICU) to remotely monitor newly intubated patients. Over the course of three months, 3196 alerts were sent in total. Of these alerts, we were able to successfully filter out 872 false alert messages by the filtering logic given in the previous section. While we filtered out most of the false alerts, it was reported by the eRTs that not all of them were filtered out. In general, these were patients that were already intubated. While it is not difficult for the eRT to ignore this message, we plan to improve our filtering logic further to distinguish between new and continued intubation.

B. Anomaly Detector

1. The anomaly detector module of VitalCore identifies the abnormal usage pattern of medical devices while avoiding raising excessive false alarms that cause alarm fatigue. We train machine learning models to learn the normal usage patterns of devices. We monitor the usage patterns of 60-second intervals, weekday, and weekend, where each pattern has its own model. Our training data is collected over five monitoring devices, which are composed of 48,096 samples of constant 60-second-intervals pattern and 6,791 samples of reduced activity after business hours on weekdays and weekends. Note, no abnormal sample is fed to the models at training. In other words, we want the models to learn the normal pattern and test their performance on abnormal instances. During testing, we provided the trained models with 48,969 samples, of which 8% are anomalous. Each model classifies each instance as anomalous or not. If any of the trained models declare a test instance to be an anomaly, we consider the classification result to be anomalous.

TABLE 1

Performance Comparison of Anomaly Detection Algorithms.

|  | ACC | F1 | PRE | REC | FPR | FNR | T |
|---|---|---|---|---|---|---|---|
| Autoencoder | 0.93 | 0.87 | 0.84 | 1.00 | 0.08 | 0.00 | 787.41 |
| 1-class SVM | 0.81 | 0.57 | 0.42 | 1.00 | 0.21 | 0.00 | 280.04 |

TABLE 1-continued

Performance Comparison of Anomaly Detection Algorithms.

| | ACC | F1 | PRE | REC | FPR | FNR | T |
|---|---|---|---|---|---|---|---|
| Matrix Profile | 0.99 | — | 0.00 | 0.00 | 0.00 | 1.00 | 295.88 |
| tsmoothie | 0.99 | — | 0.00 | 0.00 | 0.00 | 1.00 | — |

ACC: accuracy, F1: f1-score, PRE: precision, REC: recall, FPR: false positive rate, FNR: false negative rate, T: training time.

To choose the most suitable anomaly detection algorithm for each application of VitalCore, we tested four state-of-the-art algorithms, namely convolutional autoencoder [17], one class SVM [18], matrix profile and tsmoothie [20], and evaluate their performance as shown in Table 1. We chose these algorithms because they are benchmark algorithms used for unsupervised time-series anomaly detection. One-class SVM sacrifices accuracy for efficiency in run time. Matrix profile gives higher accuracy with a longer run time. Tsmoothie runs offline hence the time is not listed here for comparison. Matrix profile and tsmoothie give zero for precision, recall, and false positive rate, because they do not fit our dataset well and fail to predict any anomaly. Overall, the convolutional autoencoder provides the best performance for our application as it exhibits the minimum false alarm rate while performing highly in overall accuracy, recall, and false-negative rate.

VI. CONCLUSION

In this document, we presented VitalCore, a medical device integration platform that supports clinical decisions by reducing the manual documentation of medical device data and providing access to real-time, accurate data in the EHR. We deployed VitalCore in three real world applications at Penn Medicine: Medical Dashboard, Ventilation Alert, and Anomaly Detector. After evaluation, we found that VitalCore reduced the amount of time required of medical professionals, clinical engineers, and IT analysts by up to six times when troubleshooting. Further, we could accurately and in real time extract ventilation information and alert appropriate personnel. Finally, we detected anomalies in device usage to change troubleshooting responses from reactive to proactive.

Figure 6:
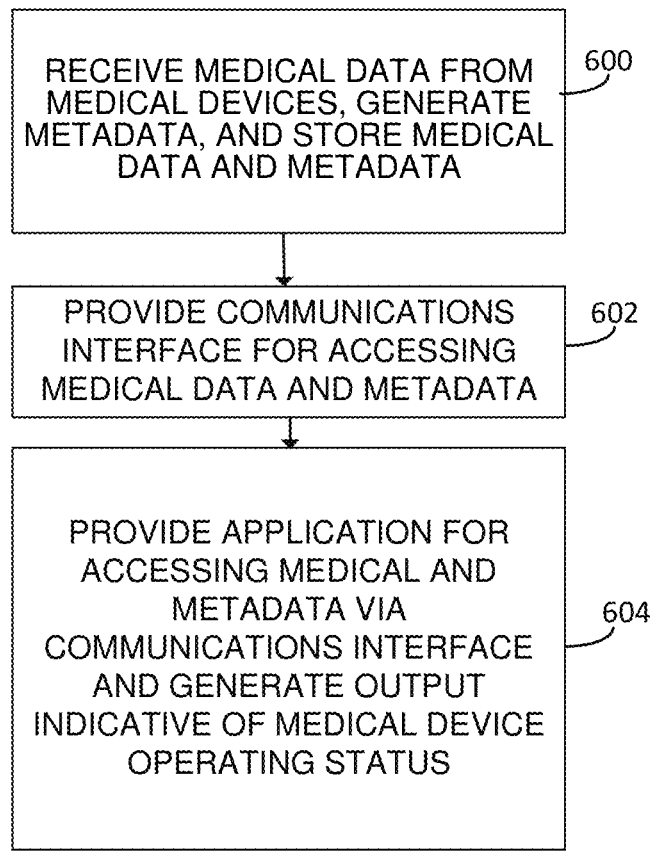
FIG. 6 is a flow chart illustrating an exemplary process for managing groups of medical devices.

FIG. 6 is a flow chart illustrating an exemplary process for medical device management. Referring to FIG. 6, in step 600, the process includes receiving medical data from a plurality of medical devices, storing the medical data, and generating and storing metadata for each of the devices. For example, the stream processor illustrated in FIG. 1 may receive medical data, such as HL7 data, from medical devices or from a middleware layer that generates the HL7 data from data received from the medical devices. The stream processor may generate timestamp metadata and other metadata from the received HL7 data and store the HL7 data and the metadata.

In step 602, the process includes providing a communications interface for granting access to the medical data via at least one communications protocol. For example, the VitalCore system illustrated in FIG. 1 may implement a REST API and a sockets API to provide access to the medical device data and the metadata.

In step 604, the process includes providing an application for accessing the medical data and the metadata via the communications interface and generating, based on the medical data and the metadata, output indicative of operating status of the medical devices. For example, the VitalCore system may include one or more applications, such as the medical device dashboard, the anomaly detector, or the ventilation alert application illustrated described above to generate output based on the medical data and the metadata.

Figure 7:
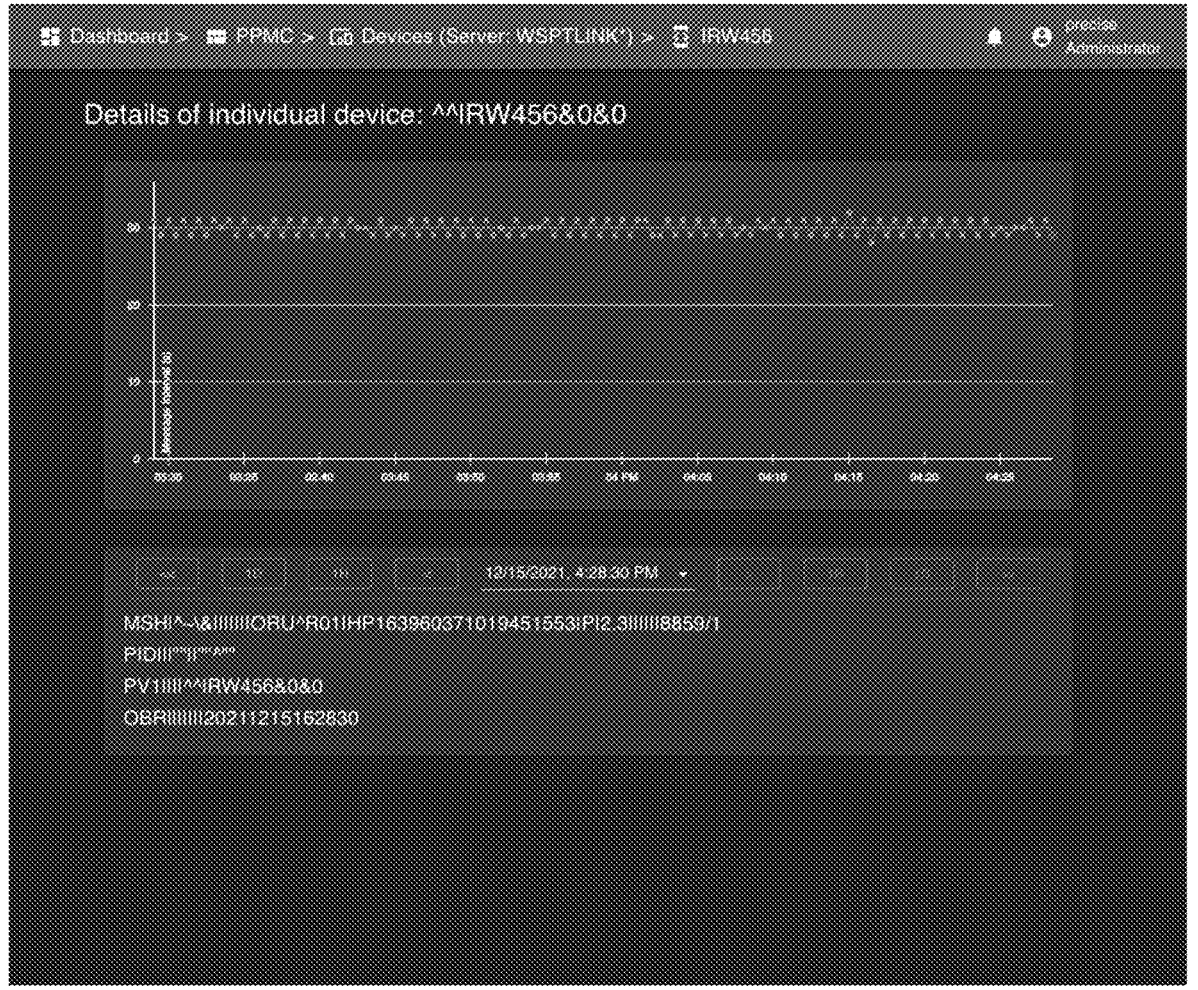
FIGS. 7-9 are computer screen shots illustrating exemplary graphical displays that may be generated by the medical device dashboard application.
Figure 8:
Figure 9:
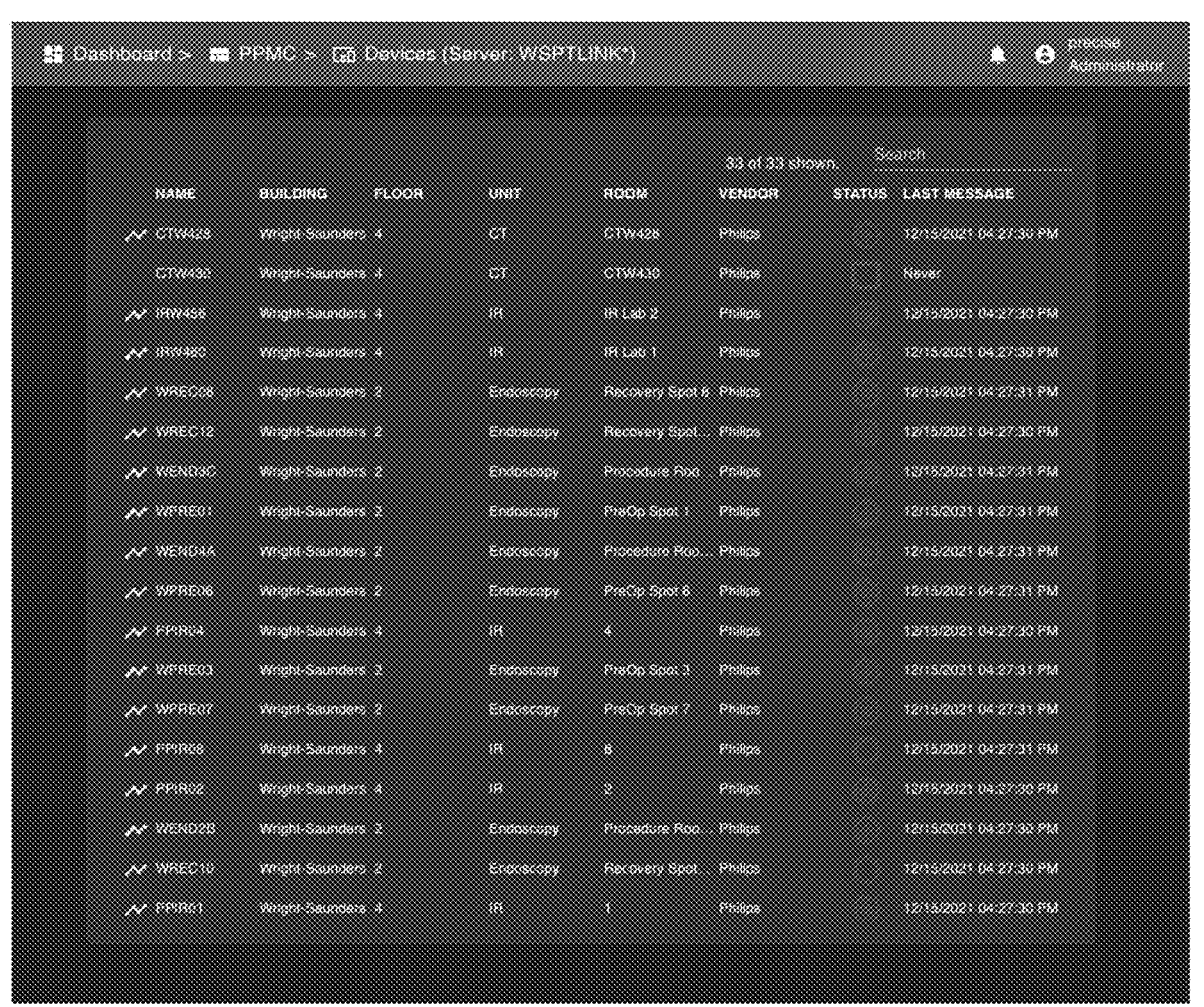

FIGS. 7-9 are computer screen shots illustrating exemplary graphical displays that may be generated by the medical device dashboard application. More particularly, FIG. 7 is a graph illustrating time between messages for an individual medical device and the HL7 data for a message generated at a particular time. As indicated in FIG. 7, the time between messages is near 30 on the graph. If the time were to decrease below a threshold, the dashboard application may generate an alert message to check the status of the medical device.

The computer screen shot of FIG. 8 illustrates numbers of active and total medical devices per server. The circles at the top of FIG. 8 each represent a group of medical devices connected to the same server. For example, the first circle on the left indicates that 32 of 33 Philips medical devices connected to a server called WSTPLINK* are active. The graph in the bottom part of the screen shot displays numbers of active medical devices over time. For example, the purple line indicates that the number of active medical devices connected to the server WSTPLINK* remains constant at 32 over the measurement interval. A sudden decrease in the number of active medical devices connected to a server, such as the drop from about 25 to 0 active medical devices for the server named PCMDBS* may indicate a server outage and result in the generation of an alert.

The screenshot of FIG. 9 is similar to the dashboard of FIG. 3A where device name, location, vendor, operating status, and last message received are displayed.

Incremental Anomaly Detection with Guarantee in the Internet of Medical Things

The Internet of Medical Things (IoMT), aided by learning-enabled components, is becoming increasingly important in health monitoring. However, the IoMT-based system must be highly reliable since it directly interacts with the patients. One critical function for facilitating reliable IoMT is anomaly detection, which involves sending alerts when a medical device's usage pattern deviates from normal behavior. Due to the safety-critical nature of IoMT, the anomaly detectors are expected to have consistently high accuracy and low error, ideally being bounded with a guarantee. Besides, since the IoMT-based system is non-stationary, the anomaly detector and the performance guarantee should adapt to the evolving data distributions. To tackle these challenges, we propose a framework for incremental anomaly detection in IoMT with a Probably Approximately Correct (PAC)-based two-sided guarantee, guided by a human-in-the-loop design to accommodate shifts in anomaly distributions. As a result, our framework can improve detection performance and provide a tight guarantee on False Alarm Rate (FAR) and Miss Alarm Rate (MAR). We demonstrate the effectiveness of our design using synthetic data and the real-world IoMT monitoring platform VitalCore.

1 INTRODUCTION

Internet of Medical Things (IoMT) is formed with medical devices, embedded software, network capabilities, and physical dynamics of the patient body [33]. Closely monitoring the physiological information of patients, IoMT provides significant benefits for the well-being of patients by increasing the quality of life and cutting medical expenses [20]. With the aging population and increasing number of patients with chronic diseases, we witness an enormous need for IoMT. Since IoMT interacts with the patients directly, the medical community imposes rigorous requirements for its usage. Specifically, IoMT-based systems must be reliable. It should function as expected at all times and not be prone to unexpected failure under normal operating conditions. Besides, the clinicians mandate the reliability of every system component to guarantee the correctness of collected information for diagnostic functions [28].

Therefore, anomaly detection is essential for the reliability of the IoMT-based system. An anomaly detector is tasked with raising alarms when an observation deviates from the normal pattern. For it to be helpful, the classification accuracy should be high, and the error rates should be low [30]. Nevertheless, for a safety-critical system like IoMT, more than average performance is required. There may still be a situation when the error rates suddenly spike, resulting in potentially hazardous patient outcomes. Therefore, a guarantee of the upper bound on the error rates should be in place to assure the system's reliability. Furthermore, for anomaly detection in IoMT, the normal and anomalous patterns evolve dynamically due to the change in usage condition, for example, patient behavioral variation and operational fluctuation [25]. Hence, anomaly detectors in IoMT-based systems should incrementally perform classification with high accuracy and tight guarantee.

We focus on addressing anomaly detection problems in IoMT with evolving usage patterns. For example, as medical technicians encounter more occurrences of regular maintenance, a type of anomaly that is non-actionable [55], they may no longer perceive the anomaly as anomalous. In other words, although the anomalous pattern persists, they treat it as normal. However, the shift in classification could drastically impair the original anomaly detector's performance and the guarantee's usefulness since they are developed oppositely.

Previous works for incremental anomaly detection span various applications, for example, network intrusion detection [21, 60], forest fire risk prediction [45], airspace operations [27]. However, most of them do not provide performance guarantees in incremental settings. Many uncertainty quantification techniques [19] provide a guarantee. Such techniques often assume a representative calibration data set of the actual data distribution to derive the guarantee [37, 38, 58, 59]. Nevertheless, anomalies could be versatile in practical settings, and the chances are that one calibration set cannot capture all the anomaly distributions. Furthermore, as people observe more incidents of a type of anomaly, the definition of the anomaly may be revised to become normal.

Figure 10:
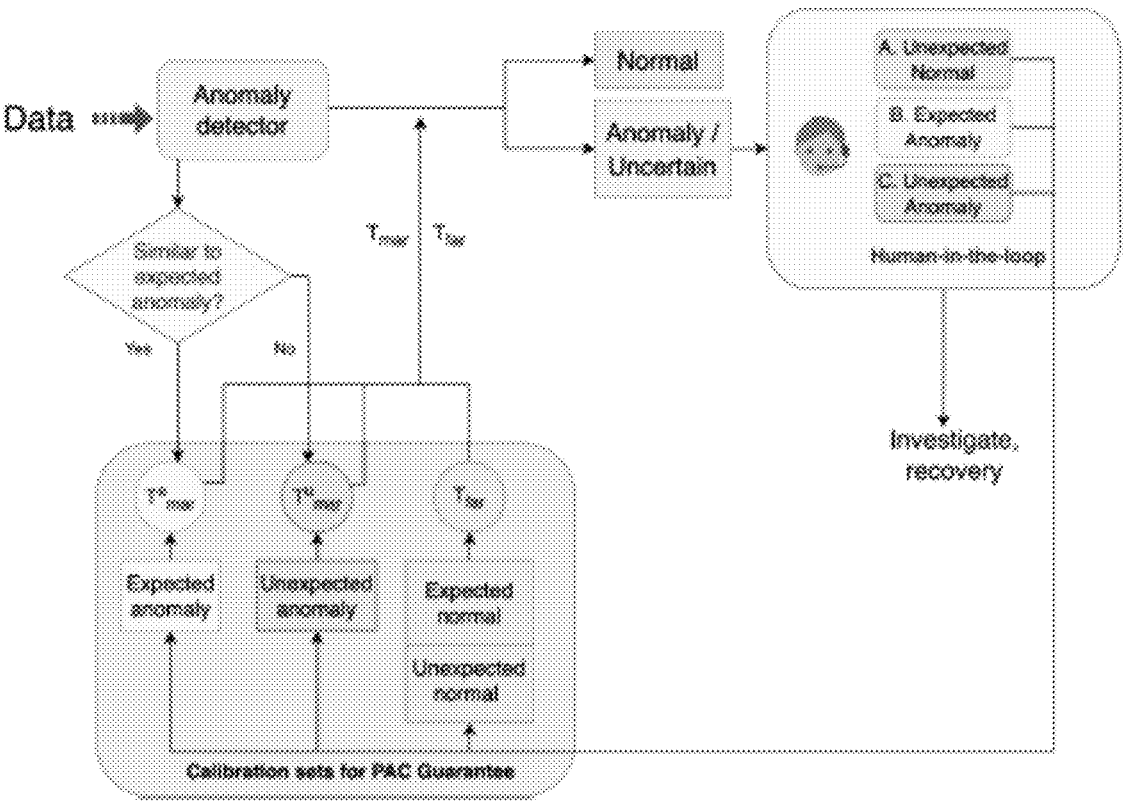
FIG. 10 is a block diagram illustrating our framework, which uses historical data to create calibration sets. New data is fed through an anomaly detector, which compares it to the expected and unexpected anomaly calibration sets. The resulting anomaly score is compared to the thresholds Tmar and Tfar, which guarantee Miss Alarm Rate (MAR) and False Alarm Rate (FAR), respectively. If the instance is classified as an anomaly or uncertain, human expertise is consulted. The calibration sets are then updated based on user feedback, and new Probably Approximately Correct (PAC) thresholds are computed for the next instance.

In this work, we propose a framework shown in FIG. 10 that provides a Probably Approximately Correct (PAC)-based guarantee for incremental anomaly detection in IoMT. Our framework adopts a human-in-the-loop design, which adapts to the user feedback on the evolving anomaly categories, i.e., expected and unexpected anomalies. With this flexible design, the user can assign the frequently observed anomalies to a calibration set of expected anomalies. Besides, they can progressively expand the unexpected anomaly categories as they discover additional types. As a result, the anomaly detection accuracy is not hampered, along with a confined performance guarantee on False Alarm Rate (FAR) and Miss Alarm Rate (MAR). The two error rates are essential for gauging the anomaly-detecting capability. Miss alarm characterizes missing an actual anomaly, whereas false alarms cause alarm fatigue if there are too many of them. Both have undesirable consequences and, thus, should be minimized for life-critical systems like IoMT.

In summary, our contributions are as follows:

Propose an incremental framework for detecting expected and unexpected anomalies with guarantee in IoMT.

Improve the classification accuracy and performance guarantee on FAR and MAR of the underlying anomaly detector.

Perform an update frequency analysis to show that the framework requires limited user input.

Evaluate the framework on synthetic data and an IoMT platform (VitalCore) to validate the effectiveness.

The remainder of this document is structured as follows. First, we start with a literature review in Section 2. Then, we elaborate on the detail of our framework in Section 3 and demonstrate the experimental results of our framework in Section 4. Finally, in Section 5 we discuss the limitation of our framework and conclude the work in Section 6.

2 RELATED WORK

2.1 Incremental Anomaly Detection

Learning-enabled anomaly detectors in IoT need to evolve continuously to adapt to operational variations as new patterns are emerging [35], which is often referred to as incremental anomaly detection [23]. It has broad applications in different domains, for example, network Intrusion Detection Systems (IDSs) [21, 60], system log analysis [22], forest fire risk prediction [45], airspace operations [27, 61], and healthcare [42]. Many online algorithms have been proposed to detect anomalies in ever-changing time series, some have a tree-based structure like Half Space Tree [44], and some are cluster-based with Gaussian Mixture Model (GMM) as the backbone [24, 30, 61]. However, most algorithms do not provide a performance guarantee, which is essential for a life-critical system like IoMT.

2.2 PAC Guarantee

Probably Approximately Correct (PAC) guarantees [38, 58] aim to give a bounded false detection rate for neural networks, based on two user-specified inputs, namely, confidence parameter $\delta$ and error parameter $\epsilon$. There are two fundamental false detection error rates in anomaly detection tasks, i.e., FAR and MAR, interchangeably called false-negative and false-positive rates. PAC-Wrap [34] proposes a wrapper around existing anomaly detectors to provide a rigorous PAC guarantee on FAR and MAR. However, there might be multiple anomaly types in practice, for example, expected or unexpected anomalies. Hence, we cannot simply adopt a binary differentiation of anomaly or normality as in [34]. We seek to consider the evolving nature of anomalies and address the problem by adopting a more fine-grained classification of anomalies.

2.3 Dataset Shift Problem

There has been abundant literature studying the dataset shift problem [41], which assumes that the testing data distribution is different from the training data distribution. Some works [46, 51, 52] provide performance guarantees on a more straightforward dataset shift problem—covariate shift problem. It assumes the training input points and test input points follow different distributions. However, the conditional distribution of output values given input points is unchanged. Researchers use the Importance Weight [53] to estimate the target distribution from a source distribution and then perform PAC guarantee [39] on top of the estimation. There is a subtle difference between our problem and dataset shift detection. Firstly, training is not demarcated from testing in our setup since testing instances could be included in the training set for future performance guarantees. Secondly, we assume that there is more than one anomaly distribution. Some of the test time anomalies might follow the same distribution as the training time.

2.4 User-Feedback for Recalibration

There are, in general, three ways to perform the recalibration: supervised, semi-supervised, and unsupervised [44, 49, 56, 62]. In our work, we propose to resort to limited user feedback for an update, which may be closest to the semi-supervised definition [29, 36, 43, 50]. A close work [49] also adopts interactive user update to improve detection accuracy. It differs from ours because we aim for high accuracy and, more importantly, a guaranteed error rate. Besides, they leverage two methods to incorporate user updates: metric learning and the Bayesian method. However, the metric learning method [49] is impossible with a vast number of data points. We cannot enumerate all data pairs and instantly compute the pairwise distance for a large dataset. Hence, we compare our framework with their Bayesian update method in Section 4.3.

3 METHOD

In this section, we describe our framework in detail. First, we formulate the problem of providing a two-sided guarantee. We then explain the PAC guarantee we provide, obtained using the PAC threshold to stratify the anomaly score. After that, we give a motivating example of why we need user feedback to split the anomaly calibration sets into more fine-grained ones. Then, based on the thresholds, we explain how to guarantee FAR and MAR. In addition, we explain how our method can guarantee high accuracy without demanding laborious user input. Finally, we discuss the implementation of our framework.

3.1 Problem Formulation

Let X be the input space, Y be the finite label space, and x,y come from the two spaces, respectively; let D denote a distribution over X×Y. We assume a semi-supervised setup with many unlabeled normal instances and a small number of labeled instances. We denote y=0 to be normal and y=1 to be anomalous. Notice that there could be more than one type of anomaly, but to evaluate the anomaly detection accuracy, we treat all of them as y=1. Our goal is to provide a prediction $\hat{y}$ for a test instance x, with FAR and MAR being upper-bounded by an error parameter $\epsilon$. Formally, we want the following:

$$FAR = \frac{\mathbb{P}_{(x,y)\sim\mathcal{D}}(\hat{y} = 1 \mid y = 0)}{\mathbb{P}_{(x,y)\sim\mathcal{D}}(\hat{y} = 1 \mid y = 0) + \mathbb{P}_{(x,y)\sim\mathcal{D}}(\hat{y} = 0 \mid y = 0)} \quad (1)$$

$$= \mathbb{P}_{(x,y)\sim\mathcal{D}_n}(\hat{y} = 1) \le \epsilon$$

where $D_n$ is the distribution of normal data. Besides, we also want:

$$MAR = \frac{\mathbb{P}_{(x,y)\sim\mathcal{D}}(\hat{y} = 0 \mid y = 1)}{\mathbb{P}_{(x,y)\sim\mathcal{D}}(\hat{y} = 0 \mid y = 1) + \mathbb{P}_{(x,y)\sim\mathcal{D}}(\hat{y} = 1 \mid y = 1)} \quad (2)$$

$$= \mathbb{P}_{(x,y)\sim\mathcal{D}_a}(\hat{y} = 0) \le \epsilon$$

where $D_a$ is the distribution of anomalous data.

3.2 PAC Thresholds

We adopt the generalization bounds for detection error from [38], which leverages PAC learning theory to construct confidence sets for anomaly detectors with PAC guarantee—i.e., the confidence set for a given input contains the true label with high probability. It is accomplished via constructing the confidence set C(x) based on a one-dimensional parameter T on the probability forecaster $f: X \mapsto \to \mathbb{R}$. In detail, we first sort the data in the calibration set according to the score output by f in ascending order, and use the score at position k*+1 as the threshold, where k* and the corresponding threshold $\hat{T}$ are calculated as follows:

$$k^* = m\alpha(m, e, \delta) \quad (3)$$

$$\hat{T} = -\log[f(y_{k^*+1} \mid x_{k^*+1})] \quad (4)$$

Specifically, in the confidence set $C_{\hat{T}}(x)$, we only include the y with a probability greater $$C_{\hat{T}}(x) = \left\{ y \in \mathcal{Y} \mid f(y \mid x) \ge e^{-\hat{T}} \right\}.$$

We can treat the anomaly detector as a probability forecaster f. Namely, we provide the PAC guarantee to the anomaly prediction result using the threshold $\hat{T}$ on the anomaly score, computed from an anomaly detector f that forecasts the probability of an instance being anomalous. Formally, given the dataset (x,y)~D, a calibration set $Z_{cal}$ with m data points, and $\epsilon$, $\delta \in \mathbb{R}$ >0, we obtain a PAC confidence set $C_{\hat{T}}(x)$ for y, satisfying the guarantee:

$$\mathbb{P}_{Z_{cal}\sim\mathcal{D}^m}\left[\mathbb{P}_{(x,y)\sim\mathcal{D}}\left(y \in C_{\hat{T}}(x)\right) \ge 1 - \epsilon\right] \ge 1 - \delta. \quad (5)$$

One can always replace the $\mathbb{P}_{(x,y)\sim\mathcal{D}}(y \in C_{\hat{T}}(x))$ with other criteria and compute the threshold accordingly. It will then guarantee the corresponding accuracy or error metrics, and we will elaborate on this in Section 3.3.

3.3 Two-Sided Guarantee

We train an anomaly detector f on a training set Ztrain consisting of solely normal instances. We maintain labelled calibration sets $Z_{cal}=\{Z_n, Z_{a1}, Z_{a2}, \ldots, Z_{ak}\}$, where $Z_n$ means a calibration set for normal data, and $Z_{ai}$, i=1, $\ldots$, k are the calibration sets for different anomaly types. To guarantee both the MAR and FAR, the two standard error rates for alarm-issuing applications, we replace the inner part of the formula as in PAC-Wrap [34]. Expressly, on the calibration set consisting of m normal data points $z_n$, we compute the threshold $\hat{T}_{FAR}$ far to guarantee FAR:

$$\mathbb{P}_{Z_n \sim \mathcal{D}_n^m}\left[\mathbb{P}_{(x,y) \sim \mathcal{D}_n}(\hat{y} = 1 \mid y = 0) \le e\right] \ge 1 - \delta. \qquad (6)$$

Similarly, on the anomalous calibration set Zai with m data points, we compute the threshold $$\hat{T}_{mar}^{ai}$$

to guarantee MAR on each anomaly type:

$$\mathbb{P}_{Z_{a_i} \sim \mathcal{D}_{a_i}^m}\left[\mathbb{P}_{(x,y) \sim \mathcal{D}_{a_i}}(\hat{y} = 0 \mid y = 1) \le e\right] \ge 1 - \delta. \qquad (7)$$

According to [38], the thresholds T^far and T^ai mar are the solution to Equation (6) and (7). In a high level, it bounds the MAR and FAR below a calibration loss function $\alpha(m, \epsilon, \delta)$, which enforces the $\epsilon$-error and $\delta$-confidence constraint.

Then, we let $\hat{T}_{MAR}$ be the threshold from the closest anomaly calibration set. Together with the threshold $\hat{T}_{FAR}$ from the normal calibration set, we can output a guaranteed prediction. Typically, the threshold $\hat{T}_{MAR}$ should lay above $\hat{T}_{FAR}$ since the former is calculated from anomalous data that have higher anomaly scores. However, the reverse scenario may occur when the anomalies cannot be easily distinguished from the normal data. We can incrementally relax the $\epsilon$ constraint or the $\delta$ constraint to allow for a more considerable error margin or lower the confidence until $\hat{T}_{MAR}$ is above $\hat{T}_{FAR}$.

Using the two thresholds together, we guide our decision by declaring anything above the $\hat{T}_{MAR}$ to be an anomaly and anything below $\hat{T}_{FAR}$ to be normal. Formally, using the two thresholds, we guide our decision for determining anomaly as follows:

$$\hat{y} = \begin{cases} 1 & f(x) \ge \hat{T}_{mar} \\ \{0, 1\} & \hat{T}_{far} < f(x) < \hat{T}_{mar} \\ 0 & f(x) \le \hat{T}_{far} \end{cases} \qquad (8)$$

Following this rule, both MAR and FAR will be guaranteed for the anomaly prediction result. If the anomaly score falls in between the two thresholds, we abstain from making predictions and resort to user feedback in this instance. Ideally, there should not be many instances with an anomaly score between the two thresholds, and the region between the two thresholds is referred to as uncertainty region. In Experiment 4.6, we conducted an ablation study to inspect the relationship between the fraction of data points that fall in the uncertainty region and the two user-specified parameters $\epsilon$ and $\delta$. Then, if the user demands a concrete decision and $\hat{T}_{MAR}$ is above $\hat{T}_{MAR}$, we can use the mean value of the two thresholds as the final threshold to guide our decision, while still maintaining the two-sided guarantee according to [34].

3.4 Fine-Grained Anomaly Calibration Sets

As we discussed earlier, the real-world anomaly distribution may be evolving; if we apply a static classification of anomalies, the user would provide the imprecise classification. As a result, the effectiveness of the guarantee we can provide will be hamstrung. An illustrating example is as follows.

For the IoMT, we monitor using VitalCore, the maintenance would suspend the system and trigger an anomalous pattern of disconnection, which is observed as a spike in time interval between two consecutive messages. The pattern is very different from normal patterns, which have a consistent time interval of around 60 seconds between two messages.

Hence, the maintenance is predicted as an anomaly by the anomaly detector. Since we do not have the up-to-date maintenance schedule, we cannot remove the maintenance data. Besides, the technicians want to keep the maintenance data to confirm that the maintenance happens as expected. We prompt the user to decide on the category for the maintenance data. Initially, we apply a static classification of anomalies, maintaining a single anomaly calibration set and a normal calibration set. After seeing some maintenance instances, the user regards them as expected and prefers not to be bothered by the alerts on such events. As a result, the user assigns maintenance instances to the normal calibration instead of the anomalous one. However, this assignment contaminates the normal training and calibration set by mixing different data distributions, disabling us from providing a high classification accuracy and a meaningful guarantee, as we show in Experiment 4.2 and Experiment 4.3. We can avoid the trivial guarantee by modifying the original classification criteria to adapt to the change. In other words, instead of predicting an instance to be either anomaly or a normal instance, we incorporate the user's perception and create a new class of anomaly—expected anomaly. Although the users are not directly involved in the calibration process, they are prompted to provide labeling on anomalies and uncertain examples. For anomalies caused by maintenance, we include them in the newly created calibration set for the expected anomaly. The adjustment in classification criteria might affect the existing calibration set. The historical calibration set could be updated by migrating or deleting the records to reflect the change. Compared with a single anomaly type, the fine-grained calibration sets with more anomaly types significantly improve the precision of the guarantee. We illustrate this example with Experiment 4.3.

We compute the PAC threshold for each fine-grained anomaly calibration set ai. Then, when an instance arrives, we choose the most appropriate anomaly calibration set $\hat{a}_i$ for it by taking the one with minimal Euclidean distance $\hat{a}_i$ between the instance and the centroid of the anomaly calibration set.

$$\hat{a}_i = \operatorname*{argmin}_{a_i} \sqrt{\left(x - \mu_{a_i}\right)^2} \qquad (9)$$

If there is more than one calibration set with the same minimal Euclidean distance, we choose the one with a smaller index. A side benefit of splitting the calibration set is the reduction in computation time of the PAC thresholds, which scales almost linearly with the calibration set size, as we will show in Experiment 4.5. In addition, since the threshold of different anomaly types are independent of each other, we can conduct the calculation parallelly on different machines, increasing the computational efficiency. Although we illustrate our result with two anomaly types, namely, the expected anomaly and the unexpected anomaly, there could be more fine-grained anomaly sub-types in practice. For example, we can treat different attack types as the sub-types of unexpected anomalies in the network intrusion detection [32]. There could be multiple sub-types of anomalies as the user defines, for example, Denial of Service (DOS) attack, R2L attack, U2R attack, probing attack and many more. Our framework can be flexibly generalized to multiple anomaly sub-types, as illustrated in Experiment 4.5.

3.5 Update Frequency

Suppose the prediction on an instance turns out to be anomalous or uncertain. In that case, we seek help from the user, with the options of approving or modifying the current label of the anomaly instance. Note that we only update the calibration set with the labeled instances. It is natural to question the practicability if a system frequently requires the user to provide feedback. Especially in the medical domain, clinicians and technicians are concurrently tasked with numerous monitoring duties. Fortunately, our framework only requires infrequent user feedback to generate a stable PAC guarantee. To start with, suppose the user is busy and can only respond to a limited number of alerts. Specifically, for every c alert(s), the user provides a label for any of them and misses the rest. The update frequency (F) is then defined as the inverse of the number of alerts generated and:

$$F = \frac{1}{c}.$$

Let t be the total number of alerts generated in the period we monitor. We have a labeled calibration set of the size $$m = m_0 + F_t = m_0 + \frac{t}{c},$$

where $m_0$ is the initial calibration set size. Notice that F=0 is defined as no update, and we use the maximal anomaly score from the training set as the threshold.

Update frequency affects the guarantee via the calibration loss. Specifically, we have a larger calibration set as we update more frequently. The increased calibration set size leads to a larger allowed calibration loss, denoted as $\alpha(m, \epsilon, \delta)$. This is because $\alpha(m, \epsilon, \delta)$ is an increasing function of calibration set size$_m$ [38]:

$$\alpha(m, \epsilon, \delta) = \epsilon \sqrt{\frac{\log(2m) + 1 - \log(\delta/4)}{m}}. \tag{10}$$

At first sight, the high frequency increasing the calibration loss might seem counter-intuitive since we normally expect increasing the effort to result in something beneficial. However, it should be alternatively interpreted as raising the selectiveness of $C_{\hat{f}}(x)$. As we have a higher a, we have a larger k* by Equation (3). Since we sort the anomaly score f $(y_k|x_k)$ in ascending order, we have a smaller $\hat{T}$ and larger $e^{-\hat{T}}$ with a larger k* by Equation (4). With a larger threshold $e^{-\hat{T}}$, we include less label y to the confidence set $C_{\hat{f}}(x)$ on average. Therefore, a high update frequency is favorable because it creates a more refined confidence set, which reduces the likelihood of getting a trivial $C_{\hat{f}}(x)$ containing all the labels in Y, i.e., $C_{\hat{f}}(x)=\{0, 1\}$. Moreover, there is a decreasing marginal effect in the update frequency or, equivalently, the calibration set size. Taking a first-order derivative of Equation (10), we get:

$$\frac{d\alpha(m, \epsilon, \delta)}{dm} = \frac{\log(2m)}{2m^2 \sqrt{\frac{\log(2m) + 1 - \log(\delta/4)}{m}}}$$

Figure 11A:
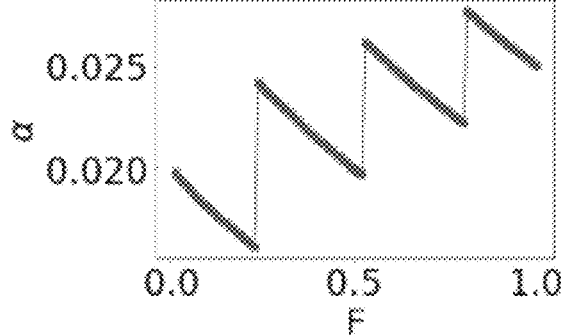
FIGS. 11A-11C are graphs illustrating the relationship between F and $\alpha$.
Figure 11B:
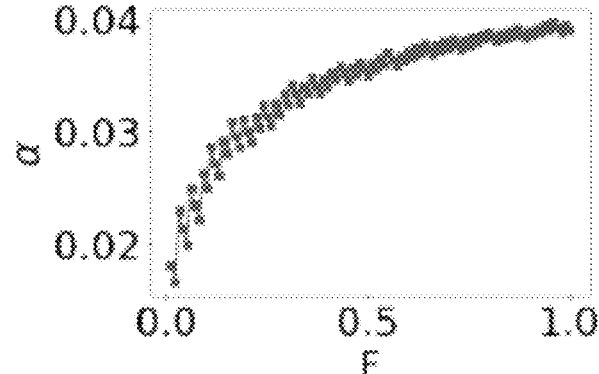
Figure 11C:
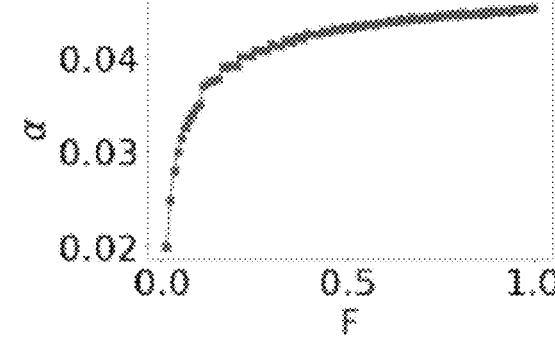

The derivative in Equation (11) is positive for m≥1 and then converges to zero as we increase m. Specifically, as we update more frequently, the confidence set shrinks less beyond a point. We visualize the relationship between frequency F and the $\alpha$ in FIGS. 11A, 11B, and 11C, given different numbers of total alerts: t=[100, 1000, 5000] with an initial calibration set size $m_0=100$, and $\epsilon=\delta=0.05$. We found that the PAC confidence set is getting more selective (a getting closer to $\epsilon=0.05$) as we update more frequently. Nevertheless, in the short run, as shown in FIGS. 11A and 11B, we could end up with a locally lower $\alpha$ as we update more frequently. According to Equation (8) in [38], larger m leads to a bigger binomial sum initially, and to satisfy the $\delta$ constraint, we must choose smaller k and hence lower $\alpha$. Overall $\alpha$ increases and the PAC confidence set gets refined as we increase the update frequency F. As shown in FIG. 11C, our framework has a decreasing return on margin regarding update frequency with t=5000. Therefore, our method does not require the user to respond to every alert generated; instead, it is sufficient to label with a frequency generating the calibration loss close to $\epsilon$. To evaluate our framework more straightforwardly, we report in Experiment 4.5 the relationship between update frequency and final accuracy of the confidence set, which ideally should have a similar pattern to that of the $\alpha$.

3.6 Implementation

Two computations are involved in providing the guarantee: the threshold computation on calibration sets and the inference on the test instance. The testing inference is a binary operation, i.e., comparing the anomaly score of the instance against the thresholds. It takes around the granularity of $10^{-5}$ s on most devices, which is undoubtedly feasible for practical deployment. The focus is on capping the size of the calibration set to compute the PAC threshold efficiently. The computation complexity of PAC is O(m), i.e., it scales linearly with the calibration set size, as we will show in Experiment 4.5. We obtain smaller calibration sets as a side benefit using fine-grained calibration sets. Besides, as we explicate the decreasing marginal effect of calibration set size in Section 3.5, the PAC guarantee does not necessitate unreasonably large data size. Users may shorten the computation time for calculating the threshold to suit their needs, as long as a minimum size of:

$$m = \frac{\log \delta}{\log(1 - \epsilon)}$$

is kept for the calibration set size. This is as little as m=59 for $\epsilon=\delta=0.05$. We implement the framework with a record pool to reflect the update frequency F. For every 1/F records accumulated in the pool, an alert is issued to the user and requests for feedback. The user can choose to provide feedback to one or multiple of the records. The ones with feedback are added to the corresponding calibration sets. The description of our framework is in Algorithm 1.

Algorithm 1: PAC Guarantee for Evolving Data
    Input: anomaly detector f, instance x, error level $\epsilon$,
        confidence level $\delta$, the user update frequency F.
    Output: anomaly prediction $\hat{y}$
    Compute $\hat{T}_{FAR}$ according to Equation (3), (4) and (6).
    Compute the $\hat{T}_{MAR}$ from the closest anomaly calibration
        set according to Equation (3), (4), (7), and (9).
    $\hat{y}$ is determined according to Equation (8).
    count=0, pool=[ ].
    if $\hat{y}{\neq}0$ then
        pool.append (x).
        count=count+1.
            if count=1/F then
                Issue an alert to the user for feedback.
                if user provide feedback y'=i (or unexpected nor-
                    mal y'=0) then
                    Add x' to $Z_{ai}$ (or $Z_n$).
                end if
                count=0, pool=[ ].
            end if
    end if
    return $\hat{y}$

4 EXPERIMENTAL RESULTS

We identified the below questions to validate the effectiveness of our framework:

Q1 Detector Improvement: how can the underlying anomaly detectors benefit from the incremental anomaly types?

Q2 Adaptive recalibration: what is the performance on the synthetic and real-world dataset using the adaptive PAC calibration sets?

Q3 Update frequency: How many alerts does the user need to provide a label for real scenarios?

Q4 Time Complexity: How does the computation time (in wall clock seconds) scale with the number of anomaly types and calibration set size.

4.1 Experimental Setup

4.1.1 Dataset

Synthetic data set: We generate the synthetic dataset with a total of 15000 data points from three 6-dimensional normal distributions $N_1$, $N_2$, $N_3$ with the same covariance matrix but with different means $\mu_1$, $\mu_2$, $\mu_3 \in$ R6. Let Ip be the p-dimensional identity matrix with p=6, and $\sigma_2$ be a uniformly random value drawn over [1,100]. Python sklearn.datasets-.make_classification library is used. We treat $N_1$ as the normal distribution, N2 as expected anomalous distribution and N3 as unexpected anomalous distribution. We have:

$$X_{normal} \sim N(\mu_1, \sigma^2 Ip)$$

$$X_{expected\ anomalous} \sim N(\mu_2, \sigma^2 Ip)$$

$$X_{unexpected\ anomalous} \sim N(\mu_3, \sigma^2 Ip).$$

VitalCore Dataset

We experiment on a 6-dimensional real-world data set that monitors the IoMT usage patterns collected on the VitalCore platform. It consists of over 3000 medical devices, and we record their connection status at the granularity of one minute. We extract six features from the records: month, day, hour, day of the week, whether in a business hour, and the interval between two consecutive records. The data we collected has three usage patterns: the connected pattern with a one-minute interval (normal), the regular maintenance pattern (expected anomaly), and the network outage pattern (unexpected anomaly). These patterns are obtained with the labels provided by the technicians. We look at the time series with a sliding window of 30 minutes upon getting the data, and the count for the number of sliding window sequences in each category is:

Normal: 418523
    Expected anomaly: 512
    unexpected anomaly: 4257

We may vary the anomaly ratio in the data to study the effectiveness of our guarantee.

4.1.2 Anomaly Detector

We employ an anomaly detector to calculate a 1-dimensional anomaly score for computing the PAC thresholds. On the synthetic data, we used a simple anomaly detector One-class Support Vector Machine [47]. On the VitalCore data, we adapt from an AutoEncoder-based anomaly detector [57], which has the best empirical prediction accuracy on VitalCore data [26]. Notice that the choice of anomaly detector is not the focus of our work since our framework is model-agnostic. It provides a two-sided guarantee for virtually any existing anomaly detector that can compute the anomaly score.

4.1.3 Metrics

We check whether the estimated FAR and MAR defined in Equation (1) and (2) are below the specified $\epsilon$ constraint. Since anomaly detection is a binary classification problem, we consider all anomaly classes as one and the normality as zero. We conducted 10 Monte Carlo trials for all experiments and reported the average result with statistical significance computed at 95% confidence level.

In Experiment 4.2, we report the Area Under the Receiver Operating Characteristic Curve (ROCAUC) and the Precision-Recall Area Under Curve (PRAUC) Score. The ROC curve is the plot of the False Positive Rate (FPR) (in the x-axis) versus the True Positive Rate (in the y-axis) across all thresholds. ROCAUC computes the Area under the ROC curve, a standard metric for comparing binary classifier models directly. However, ROC curves may provide an excessively optimistic view of the performance for imbalanced binary classification; researchers also refer to the PRAUC for a more comprehensive comparison. A Precision-Recall curve (or PR Curve) is a plot of the recall (in the x-axis) and the precision (in the y-axis) for different probability thresholds. The PR curve focuses on the minority class, making it an effective diagnostic for imbalanced binary classification models like anomaly detectors. Similarly, PRAUC summarizes the PR curve with a range of threshold values as a single score.

4.1.4 Configuration Details

Our framework is implemented using PyTorch [40]. All experiments, including timings, were run with 4 Nvidia 2080Ti GPU, 80 vCPUs, a processor Intel (R) Xeon (R) Gold 6148 @ 2.4 GHz and 768 GB of RAM.

4.1.5 Baseline

An alternative way to our way of updating the calibration set is using a Bayesian approach to update the posterior as in [49]. We could adjust the probability of an instance belonging to each anomaly type as we receive user feedback. Let P (A|B) be the posterior probability we want to update, where A denotes a data point as an anomaly, and B denotes that it is predicted as normal. Then, we follow the setup in [49] and update the probability p=P(A) whenever we receive an update from the user. Besides, we uniformly decide the environment complexity parameter q=P(B|A)=⅓. The posterior probability p is updated as follows:

$$p = \frac{P(B \mid A)P(A)}{P(B)} = \frac{qp}{1 - p(1 - q)}$$

In other words, as we receive more normal feedback from the user, we decrease the posterior probability of an instance being an anomaly. We conduct the update for the posterior of the normal whenever it is an anomaly update, whether expected or unexpected. Besides, we normalize the probability with a softmax function after each update to ensure it always remains in the [0, 1] range.

4.2 Q1 Detector Improvement

The classification accuracy of the anomaly detectors improves as they receive incremental anomaly categorization. We illustrate this by comparing the ROCAUC and PRAUC performance of the anomaly detectors with and without fine-grained anomaly distinction. We first train an anomaly detector on a training set of 5000 data points. The expected anomaly is considered normal if we have a single anomaly type. Only unexpected anomalies are considered anomalies. On the other hand, if we have two anomaly types, we distinguish expected anomaly from normality and train with only normal data. Specifically, on synthetic data, we have:

Single anomaly type: the training set contains 2500 data points from $N_1$ and 2500 data points from $N_2$.

Two anomaly types: the training set contains 5000 data points from $N_1$.

On VitalCore data, we have:

Single anomaly type: the training set contains 2500 data points with the normal connected pattern and 2500 data points with the regular maintenance pattern.

Two anomaly types: the training set contains 5000 data points from the normal connected pattern. On the testing set with 5000 data points, we randomly shuffle all data points from the three distributions and evaluate the ROCAUC and PRAUC.

Figure 12A:
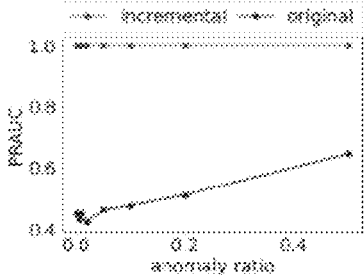
FIG. 12A-12D are graphs illustrating that PRAUC and ROCAUC performance improves with the incremental distinction of anomaly types.
Figure 12B:
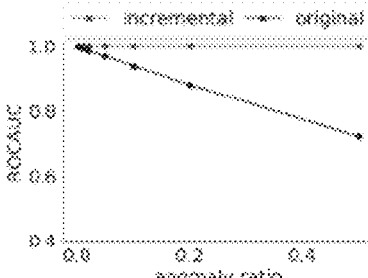
Figure 12C:
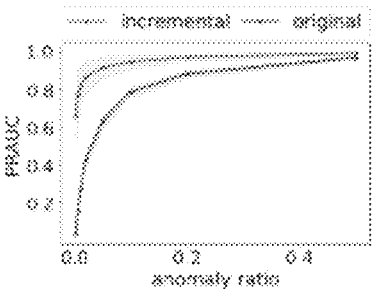
Figure 12D:
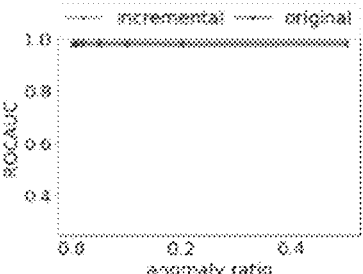

Using a single anomaly type categorization hurts the performance of the anomaly detector. An anomaly detector usually learns a homogeneous normal pattern. It classifies any data points that deviate from the pattern as an anomaly. The "contaminated" normal category confounds the anomaly detector with heterogeneous patterns. The detection performance is shown in FIG. 12A, FIG. 12B for synthetic data and FIG. 12C and FIG. 12D for VitalCore data. To validate the effect of contamination, we experiment with different anomaly ratios a. We present the original anomaly detector performance *with the blue* lines labeled "original" and the one with incremental anomaly categorization using the red lines labeled "incremental".

As shown in FIGS. 12A-12D, incremental anomaly detectors have higher ROCAUC and PRAUC. It indicates that the detection performance improves with the fine-grained classification of expected anomalies. On the synthetic data, we find the PRAUC of the original anomaly detector is close to 0.5. Therefore, mixing the expected anomaly with normal data would significantly impact the classification performance. The gap in the original ROCAUC and PRAUC reveals the imbalanced data problem. Even though we have a high ROCAUC (close to 1.0) with a small anomaly ratio, the PRAUC is low (less than 0.5). Hence, we should consider both metrics to evaluate the anomaly detection performance. As a result, adopting the fine-grained distinction would improve the PRAUC by 0.52 and the ROCAUC by 0.06 on average across different anomaly ratios.

On the VitalCore data, the PRAUC increases by 0.35, and the ROCAUC increases by 0.01 on average. In addition, we can see that the PRAUC falls below 0.5 when the anomaly ratio is smaller than 5%, indicating that the anomaly detector performs no better than random guessing on anomalies. However, a minor anomaly ratio is usually the case in reality. Fortunately, our framework can significantly improve the anomaly detector performance to have an average PRAUC greater than 0.65, even with a minuscule anomaly ratio like 0.1%.

Moreover, the PRAUC improvement is not as significant as the synthetic data when we have a large anomaly ratio above 5%. It may be because the expected anomaly pattern in VitalCore is close to the normal data. Expected anomalies are system reboots that usually recover within three minutes, and normal patterns are consistent at one-minute intervals. However, a network outage could last up to several hours. Hence, the anomaly detector may merge the expected anomaly and normal into a single cluster and classify them against the unexpected anomaly well. Despite this, the anomaly detector would still benefit from an updated anomaly categorization, especially when we have a relatively small anomaly ratio.

4.3 Q2 Adaptive Recalibration

To evaluate the effectiveness of our guarantee, we compare the performance with and without adaptive recalibration. Specifically, without recalibration, we have a single anomaly-type calibration set. However, with the adaptive change to accommodate evolving anomalies, we have two fine-grained anomaly calibration sets, i.e., expected anomaly and unexpected anomaly. Besides, we also compared our update method with a Bayesian update approach in [49].

4.3.1 Synthetic Data

On the synthetic data, we first train an anomaly detector on a training set of 5000 data points drawn from N1. Then, we simulate real-world settings to feed data into the system. We use the trained anomaly detector to compute the anomaly score on the calibration set with 5000 data points. On the anomaly score computed from the calibration set, we calculate the two thresholds:

Single anomaly type: we calculate threshold $\hat{T}_{FAR}$ from the "normal" calibration set consists of half of $N_1$ and half of $N_2$ and calculate $\hat{T}_{MAR}$ on the anomaly score of $N_3$.

Two anomaly types: we calculate threshold $\hat{T}_{FAR}$ on $N_1$ and calculate $$\hat{T}_{MAR}^{a1} \text{ and } \hat{T}_{MAR}^{a2}$$

on $N_2$ and $N_3$, respectively.

On the testing set with 5000 data points, we randomly shuffle all data points from the three distributions. For each point fed into the system, we get the anomaly score from the trained anomaly detector and use the thresholds to guide our detection:

Single anomaly type: we use $\hat{T}_{FAR}$ and $\hat{T}_{MAR}$ as calculated above.

Two anomaly types: we calculate the Euclidean distance of a data point to the calibration set centroid of $N_2$ and $N_3$ as in Equation (9). We then use the threshold of the closer one as the $\hat{T}_{MAR}$ together with $\hat{T}_{FAR}$ to determine an anomaly.

Eventually, we evaluate the final FAR and MAR on the testing set. We experiment with different levels of anomaly ratio a=[0.1%, 0.5%, 1%, 2%, 5%, 15%, 20%, 50%] while fixing the calibration set size to be 5000 and see how the PAC guarantee is affected. Initially, we set the error constraint to be $\epsilon$=0.02. Then, if it cannot be satisfied, we increment at a step of 0.1 each round until both error rates can be guaranteed below the updated $\epsilon$.

Figure 13A:
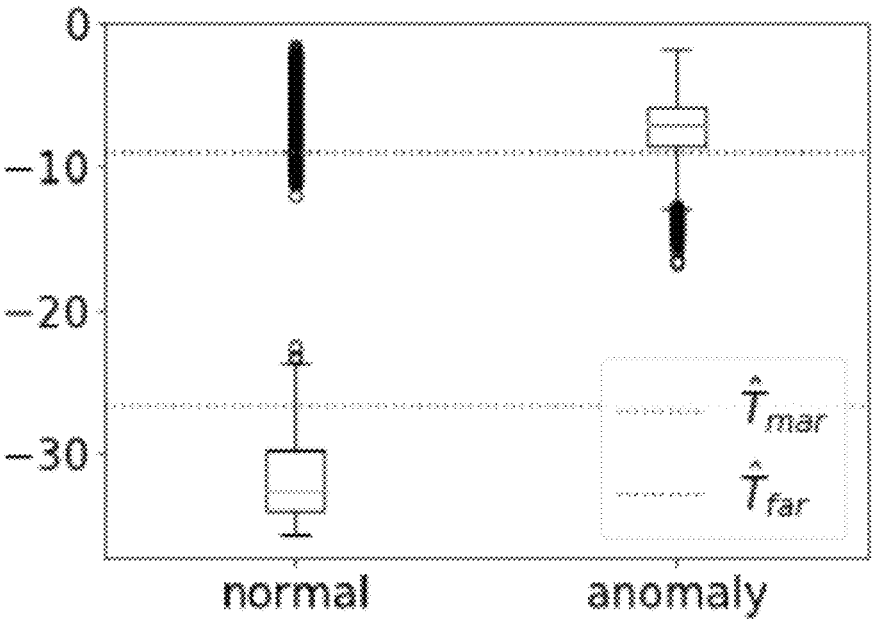
FIGS. 13A and 13B are graphs showing anomaly score distributions on the synthetic data with initial $\epsilon$=0.02, $\alpha$=0.05.

As a result, if we do not adaptively include new anomaly types, the guarantee we can provide is imprecise. The results are shown in Table 2, a denotes the anomaly ratio, e is the guaranteed upper bound for error rates, U0 is the initial uncertainty region without relaxing $\epsilon$, and U is the final uncertainty region. With a single anomaly type, the error rate we can guarantee goes from 0.02 to 0.62 with an increasing ratio of anomaly. Since column MAR and FAR are smaller than column $\epsilon$ with 95% confidence, the guarantee is satisfied. However, at the level of 0.62, we can only guarantee that there would be around half the chance that the alarm is not a false alarm or that we will not miss an actual alarm, which is of limited usefulness. FIG. 13A shows the anomaly score distribution. We can see that the normal calibration set contains both real normal instances and anomalous instances that are perceived as normal; thus, the maximal anomaly score for the normal calibration set is high.

Also, without relaxing the $\epsilon$ constraint, the uncertain region between the two thresholds contains more and more data points, i.e., from 23% to 89%, as shown in column $U_0$ of Table 2. Intuitively, it means that with more anomalies mixed up in the normal calibration set, we get more confused and abstain from predicting at the initial level of $\epsilon$=0.02, which aligns with our expectations. Therefore, we relax the error constraint incrementally to reduce the uncertainty region. As a result, the final uncertainty region in U is much smaller than $U_0$.

Figure 13B:
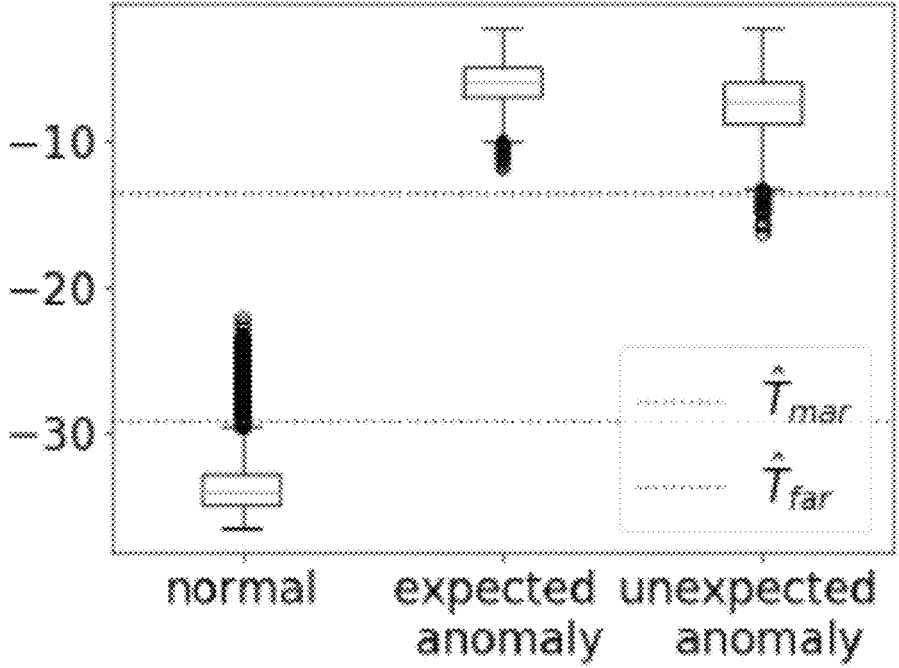

On the other hand, with the fine-grained calibration sets, the $\epsilon$ guarantee we can get is precise, i.e., $\epsilon$=0.02. The result is shown in columns $\epsilon$, $MAR_{pac}$ and $FAR_{pac}$ of Table 3, implying that using the user perception to create fine-grained anomaly calibration sets can significantly improve the guarantee we can provide to the user. Furthermore, the uncertain region U0,U between the two thresholds is consistently lower than 2%. It illustrates that we are relatively sure about the prediction with the fine-grained anomaly calibration sets. Hence, we do not abstain from making predictions on more than 2% of the test data. The anomaly score distribution for the fine-grained calibration sets is shown in FIG. 13B, and the normal calibration set contains only the actual normal instances.

The Bayesian approach, which is shown in the $MAR_{bayes}$ and $FAR_{pac}$ columns of Table 3, also meets the initial $\epsilon$=0.02 guarantee. However, our framework has a lower FAR and a comparable MAR.

4.3.2 VitalCore Data

Figure 14A:
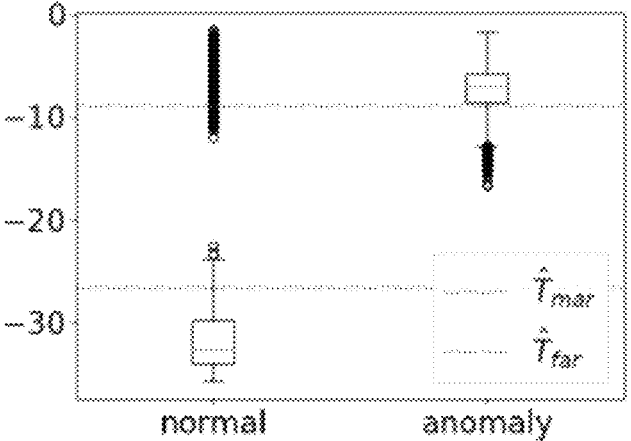
FIGS. 14A and 14B are graphs showing anomaly score distributions on the VitalCore data with initial $\epsilon$=0.02, anomaly ratio $\alpha$=0.05.
Figure 14B:
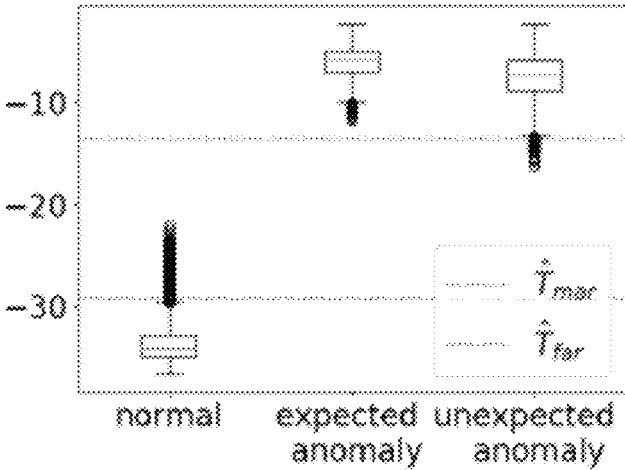

On VitalCore data, we follow the same training, calibrating, and testing procedure and data set size as the one on synthetic data. Furthermore, we observe a similar result for contaminating the normal calibration set with the expected anomalies. The results are shown in Table 4, 5, and FIGS. 14A and 14B. Using two-anomaly-type calibration sets separates the expected anomaly from normal. It enables us to have a clean normal score distribution, as shown in FIG. 14B. As a result, we have a more precise guarantee based on column $\epsilon$ of Table 4 and Table 5, i.e., from 0.12 to 0.09. However, the improvement is not as significant as in the synthetic data for a similar reason as we discussed in Experiment 4.2. Despite this, it is still advantageous to use the fine-grained calibration sets for tight control of both MAR and FAR. The uncertainty region $U_0$ also expands as we increase the anomaly ratio, mitigated as we relax the error constraint, as shown in column U.

TABLE 2

| | | Single-anomaly-type calibration set for synthetic data | | | |
|---|---|---|---|---|---|
| $\alpha$ | $\epsilon$ | MAR | FAR | $U_0$ | U |
| 0.1% | 0.02 | 0.0 ± 0.0 | 0.0015 ± 0.0 | 0.0191 ± 0.0007 | 0.0191 ± 0.0007 |
| 0.5% | 0.02 | 0.0 ± 0.0 | 0.0062 ± 0.0001 | 0.0134 ± 0.0006 | 0.0134 ± 0.0006 |
| 1% | 0.02 | 0.0 ± 0.0 | 0.0123 ± 0.0001 | 0.0057 ± 0.0007 | 0.0057 ± 0.0007 |
| 5% | 0.22 | 0.1297 ± 0.0025 | 0.2066 ± 0.0003 | 0.2291 ± 0.0004 | 0.0128 ± 0.0004 |
| 10% | 0.42 | 0.2897 ± 0.0037 | 0.3409 ± 0.0007 | 0.4004 ± 0.0005 | 0.073 ± 0.0013 |
| 15% | 0.52 | 0.3781 ± 0.0021 | 0.4239 ± 0.0009 | 0.5265 ± 0.0005 | 0.1464 ± 0.0011 |
| 20% | 0.52 | 0.4371 ± 0.0027 | 0.4826 ± 0.0012 | 0.6234 ± 0.0006 | 0.0743 ± 0.0025 |
| 50% | 0.62 | 0.6039 ± 0.0011 | 0.5921 ± 0.0009 | 0.8935 ± 0.0007 | 0.0359 ± 0.0025 |

TABLE 3

| | | Two-anomaly-type calibration sets for synthetic data, compared with the Bayesian approach. | | | | | |
|---|---|---|---|---|---|---|---|
| $\alpha$ | $\epsilon$ | $MAR_{pac}$ | $MAR_{bayes}$ | $FAR_{pac}$ | $FAR_{bayes}$ | $U_0$ | U |
| 0.1% | 0.02 | 0.0 ± 0.0 | 0.0 ± 0.0 | 0.0 ± 0.0 | 0.0004 ± 0.0 | 0.0176 ± 0.0004 | 0.0176 ± 0.0004 |
| 0.5% | 0.02 | 0.0 ± 0.0 | 0.0 ± 0.0 | 0.0 ± 0.0 | 0.0004 ± 0.0 | 0.0182 ± 0.0005 | 0.0182 ± 0.0005 |
| 1% | 0.02 | 0.0 ± 0.0 | 0.0 ± 0.0 | 0.0 ± 0.0 | 0.0004 ± 0.0 | 0.0171 ± 0.0006 | 0.0171 ± 0.0006 |
| 2% | 0.02 | 0.0 ± 0.0 | 0.0 ± 0.0 | 0.0 ± 0.0 | 0.0005 ± 0.0 | 0.0183 ± 0.0003 | 0.0183 ± 0.0003 |
| 5% | 0.02 | 0.0 ± 0.0 | 0.0 ± 0.0 | 0.0 ± 0.0 | 0.0007 ± 0.0 | 0.0171 ± 0.0004 | 0.0171 ± 0.0004 |
| 10% | 0.02 | 0.0 ± 0.0 | 0.0 ± 0.0 | 0.0 ± 0.0 | 0.0006 ± 0.0 | 0.0176 ± 0.0004 | 0.0176 ± 0.0004 |
| 15% | 0.02 | 0.0 ± 0.0 | 0.0 ± 0.0 | 0.0 ± 0.0 | 0.0001 ± 0.0 | 0.0163 ± 0.0004 | 0.0163 ± 0.0004 |
| 20% | 0.02 | 0.0 ± 0.0 | 0.0 ± 0.0 | 0.0 ± 0.0 | 0.0002 ± 0.0 | 0.0167 ± 0.0002 | 0.0167 ± 0.0002 |
| 50% | 0.02 | 0.0 ± 0.0 | 0.0 ± 0.0 | 0.0 ± 0.0 | 0.0001 ± 0.0 | 0.0136 ± 0.0002 | 0.0136 ± 0.0002 |

$MAR_{pac}$ and $FAR_{pac}$ denote the MAR and FAR using our update approach. $MAR_{bayes}$ and $FAR_{bayes}$ denote the MAR and FAR using the Bayesian approach.

The result for using the Bayesian approach on VitalCore data is shown in column $MAR_{bayes}$ and $FAR_{bayes}$ of Table 5. It manifests the benefit of having a guarantee for error rates. Although the Bayesian method generates a smaller MAR than ours, it has FAR of around 40%, violating the $\epsilon=0.09$ constraint on FAR. The high FAR would lead to ±ensures that both FAR and MAR are below the $\epsilon=0.09$ constraint, which is shown in columns $MAR_{pac}$ and $FAR_{pac}$ of Table 5.

TABLE 4

Single-anomaly-type calibration set with VitalCore data.

| α | ε | MAR | FAR | U₀ | U |
|---|---|-----|-----|------|---|
| 0.1% | 0.12 | 0.0464 ± 0.0312 | 0.0629 ± 0.0213 | 0.1121 ± 0.0636 | 0.0658 ± 0.022 |
| 0.5% | 0.12 | 0.053 ± 0.0301 | 0.0604 ± 0.0184 | 0.1279 ± 0.0799 | 0.0699 ± 0.0146 |
| 1% | 0.12 | 0.0533 ± 0.0313 | 0.0566 ± 0.0164 | 0.1177 ± 0.0566 | 0.0776 ± 0.0126 |
| 2% | 0.12 | 0.0468 ± 0.0236 | 0.0577 ± 0.0176 | 0.1126 ± 0.071 | 0.0735 ± 0.0144 |
| 5% | 0.12 | 0.0456 ± 0.0237 | 0.0598 ± 0.0191 | 0.1458 ± 0.0792 | 0.0663 ± 0.0184 |
| 10% | 0.12 | 0.0498 ± 0.0246 | 0.0596 ± 0.0189 | 0.1302 ± 0.0678 | 0.0737 ± 0.0186 |
| 15% | 0.12 | 0.051 ± 0.0263 | 0.06 ± 0.0187 | 0.127 ± 0.0552 | 0.0756 ± 0.0173 |
| 20% | 0.12 | 0.0397 ± 0.0209 | 0.0641 ± 0.0209 | 0.1492 ± 0.0617 | 0.0691 ± 0.0197 |
| 50% | 0.12 | 0.0579 ± 0307 | 0.0552 ± 0.0159 | 0.2221 ± 0.0563 | 0.0908 ± 0.014 |

TABLE 5

Two-anomaly-type calibration set with VitalCore data, compared with the Bayesian approach.

| α | ε | $MAR_{pac}$ | $MAR_{bayes}$ | $FAR_{pac}$ | $FAR_{bayes}$ | U₀ | U |
|---|---|------|------|------|------|------|---|
| .1% | 0.09 | 0.0504 ± 0.0278 | 0.0 ± 0.0 | 0.0419 ± 0.0225 | 0.4051 ± 0.0 | 0.0942 ± 0.0574 | 0.064 ± 0.0274 |
| .5% | 0.09 | 0.0398 ± 0.0213 | 0.0 ± 0.0 | 0.0465 ± 0.0259 | 0.4040 ± 0.0 | 0.1348 ± 0.0892 | 0.0591 ± 0.0269 |
| 1% | 0.09 | 0.0432 ± 0.0219 | 0.0 ± 0.0 | 0.0419 ± 0.0233 | 0.4060 ± 0.0 | 0.1057 ± 0.0708 | 0.0636 ± 0.0267 |
| 2% | 0.09 | 0.0416 ± 0.0219 | 0.0 ± 0.0 | 0.044 ± 0.0244 | 0.4060 ± 0.0 | 0.0973 ± 0.0726 | 0.0614 ± 0.0268 |
| 5% | 0.09 | 0.0387 ± 0.0204 | 0.0 ± 0.0 | 0.0485 ± 0.0283 | 0.4048 ± 0.0 | 0.1395 ± 0.0948 | 0.0554 ± 0.0291 |
| 10% | 0.08 | 0.0361 ± 0.0193 | 0.0 ± 0.0 | 0.0439 ± 0.0245 | 0.4060 ± 0.0 | 0.1074 ± 0.076 | 0.0491 ± 0.0256 |
| 15% | 0.09 | 0.0422 ± 0.0222 | 0.0 ± 0.0 | 0.0422 ± 0.0239 | 0.4039 ± 0.0 | 0.1283 ± 0.0861 | 0.0632 ± 0.0266 |
| 20% | 0.09 | 0.0453 ± 0.0238 | 0.0 ± 0.0 | 0.0405 ± 0.0223 | 0.4070 ± 0.0 | 0.0928 ± 0.0626 | 0.0636 ± 0.027 |
| 50% | 0.09 | 0.0396 ± 0.0221 | 0.0 ± 0.0 | 0.0420 ± 0.0228 | 0.4056 ± 0.0 | 0.0918 ± 0.0614 | 0.0597 ± 0.024 |

$MAR_{pac}$ and $FAR_{pac}$ denote the MAR and FAR using our update approach. $MAR_{bayes}$ and $FAR_{bayes}$ denote the MAR and FAR using the Bayesian approach.

4.4 Q3 Update Frequency

To free the user from continual labeling of the alert generated, we demonstrate that our framework does not require a high update frequency (e.g., labeling every alert). In addition, it would be sufficient for the user to label at a frequency that gives a high accuracy close to the convergence accuracy. To validate our theoretical analysis on an actual application, we experiment with the VitalCore data from April to October 2022. During these six months, the platform generates 146 alerts for 22 servers across ten hospitals. The technicians provide labels for 130 unexpected anomalies. We begin with an initial calibration set of the size $m_0=2500$, and $\epsilon=\delta=0.05$. Then, we add labeled instances to the calibration set. During expanding calibration sets, we vary the update frequency to study its effect on accuracy. Then, we evaluate the resultant accuracy on the testing set; we plot around it with a 95% confidence interval.

Figure 15:
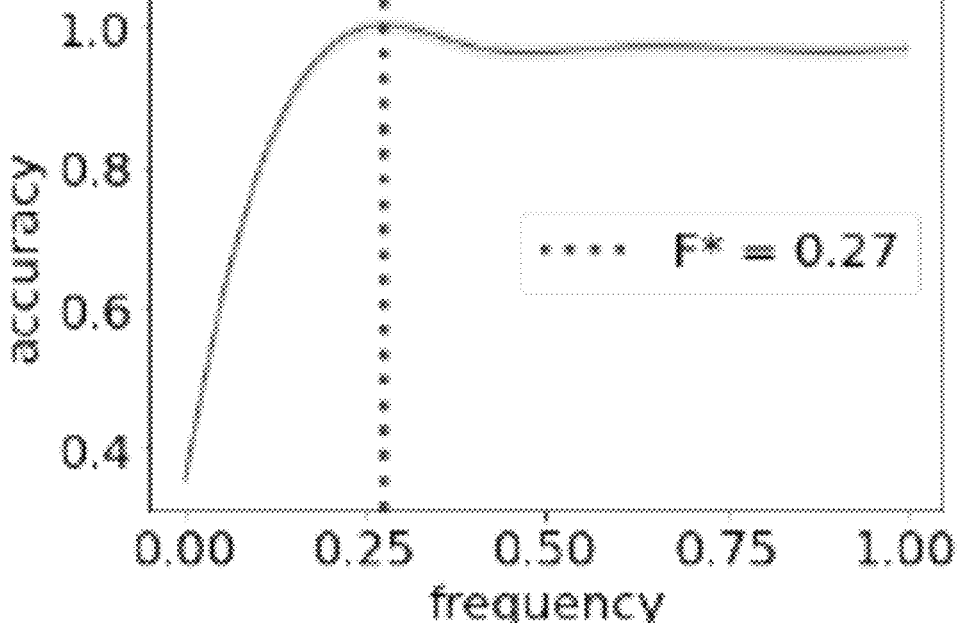
FIG. 15 is a graph of update frequency and accuracy.

The result in FIG. 15 confirms our theoretical analysis. As the update frequency reaches approximately $F^*=0.27$, equivalent to 35 alerts in real life, the accuracy stays close to perfect accuracy. Hence, there is no incentive to increase the update frequency further and provide labels to all 146 alerts. The update frequency suggests 35 anomaly labels over six months, which is approximately one label input for the anomaly per week. Moreover, the time needed to converge to a high accuracy depends on the user-specified error and confidence level. The higher the level (i.e., more relaxed), the faster we can gather enough feedback from the user and guarantee accurate performance.

TABLE 6

Calibration and test time with different calibration set sizes.

| size | calibration | test |
|------|-------------|------|
| 2000 | 0.8858 ± 0.0104 | $7.2519 \times 10^{-6} \pm 9.0409 \times 10^{-8}$ |
| 3000 | 1.3554 ± 0.0192 | $7.2484 \times 10^{-6} \pm 8.9195 \times 10^{-8}$ |
| 5000 | 2.6700 ± 0.0297 | $9.6435 \times 10^{-6} \pm 6.8809 \times 10^{-7}$ |

TABLE 6-continued

Calibration and test time with different calibration set sizes.

| size | calibration | test |
|------|-------------|------|
| 10000 | 5.0126 ± 0.0523 | $1.0513 \times 10^{-5} \pm 8.6625 \times 10^{-7}$ |
| 15000 | 7.2046 ± 0.0247 | $1.0234 \times 10^{-5} \pm 9.4843 \times 10^{-7}$ |
| 20000 | 10.1308 ± 0.2232 | $1.0529 \times 10^{-5} \pm 8.5205 \times 10^{-7}$ |

TABLE 7

Calibration and test time with different number of anomaly types.

| types | calibration | parallel | test |
|-------|-------------|----------|------|
| 2 | 5.1763 ± 0.4813 | 6.329 ± 0.5084 | $7.5182 \times 10^{-6} \pm 4.4831 \times 10^{-1-7}$ |
| 3 | 5.3526 ± 0.521 | 5.7737 ± 0.5048 | $8.9622 \times 10^{-6} \pm 5.7485 \times 10^{-7}$ |
| 4 | 5.4606 ± 0.4675 | 6.2248 ± 0.5167 | $1.0615 \times 10^{-5} \pm 1.0786 \times 10^{-6}$ |
| 5 | 5.5443 ± 0.4664 | 5.9686 ± 0.5462 | $1.2305 \times 10^{-5} \pm 1.6992 \times 10^{-6}$ |
| 6 | 5.7472 ± 0.4666 | 5.7497 ± 0.5147 | $1.3343 \times 10^{-5} \pm 1.4019 \times 10^{-6}$ |
| 7 | 5.8692 ± 0.465 | 5.6113 ± 0.5027 | $1.4792 \times 10^{-5} \pm 1.5338 \times 10^{-6}$ |
| 8 | 6.0652 ± 0.4685 | 6.1067 ± 0.5232 | $1.6849 \times 10^{-5} \pm 2.3269 \times 10^{-6}$ |
| 9 | 6.2204 ± 0.4748 | 5.6539 ± 0.5335 | $1.6838 \times 10^{-5} \pm 8.0361 \times 10^{-7}$ |
| 10 | 6.4894 ± 0.4868 | 5.8449 ± 0.5301 | $1.9270 \times 10^{-5} \pm 2.1625 \times 10^{6}$ |
| 11 | 6.6487 ± 0.5101 | 5.8172 ± 0.5221 | $2.0047 \times 10^{-5} \pm 1.2425 \times 10^{-6}$ | parallel is the time for computing the PAC thresholds with parallelization.

Total calibration set size is fixed to be 10000.

4.5 Q4 Computation Time

In this experiment, we study the scalability of our framework with different calibration set sizes and anomaly types. The experiment of varying anomaly types considers the potential distribution shift in the future, where the unexpected anomalies further evolve into more anomaly subcategories. We recorded the time needed to calculate the thresholds on the calibration set (calibration) as well as the inference time during testing (test). Specifically, we change the calibration set size and number of anomaly sub-types to see how our framework scales with them. We first describe how we generate the data for Table 6 and Table 7. To generate Table 6, we varied the calibration set size from 2000 to 20000, with anomaly ratio a=0.05. For Table 7, we generated from one to ten unexpected anomaly sub-types. Specifically, we sample data from different normal distributions with distinct means $\mu_2, \mu_3, \ldots, \mu_{11}$. Meanwhile, we fix the calibration size to be 10000 to have sufficient instances for each anomaly type. In Table 7, we started with two anomaly types in the first row (expected and unexpected) and then added one more unexpected sub-type for the next row, and so on.

In Table 6 and Table 7, we can see that the time needed to compute the threshold scales almost linearly with calibration size and the number of anomaly types. The inference time for each instance takes around 10-5 seconds, making it feasible for real-time applications. As we increase the calibration set size, we expect the test to be relatively constant. However, the test time also increases, as shown in column test of Table 6. It may be because we need more time to compute the centroid of a larger calibration set.

Furthermore, since the PAC threshold computations of different anomaly types are independent, we can distribute the workloads to several machines to curtail the linear growth. The result is shown in column parallel of Table 7. However, the benefit of parallelization is not very obvious when we have less than nine anomaly types due to the computation overhead.

4.6 Q5 Ablation Study

Figure 16:
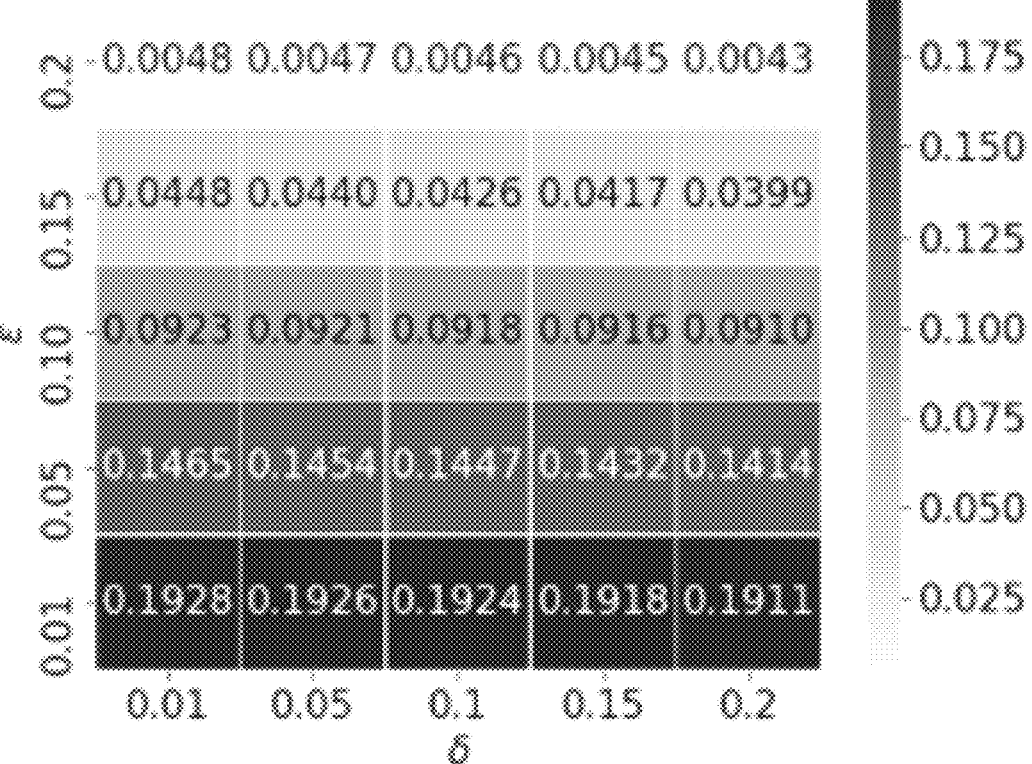
FIG. 16 is a graph of the mean uncertainty region with different values of specified $\epsilon$ and $\delta$.

FIG. 16 shows the mean uncertainty region with different values of user-specified $\epsilon$ and $\delta$. It is computed on VitalCore data with its original anomaly ratio a=0.05, and we perform no recalibration. The uncertainty region increases as we impose a more stringent requirement on error and confidence levels, revealing a trade-off between the requirements and uncertainty region. Additionally, the uncertainty is predominately affected by $\epsilon$ rather than $\delta$. Therefore, we can shrink the uncertainty region by relaxing the $\epsilon$, $\delta$ constraint or vice versa.

DISCUSSION

One obvious concern regarding the feasibility of our framework is prompting the user for feedback. The usefulness of our framework will naturally be challenged if it needs laborious user input. However, in experiments on the VitalCore platform in real scenarios, the technicians are satisfied with providing at least one label for each anomaly type weekly. The frequency sustains the anomaly detection performance and obtains a minimum performance guarantee.

The trade-off between the user input and the tightness of the guarantee is that the PAC guarantee is asymptotic. As we obtain more data points, we are more certain about the underlying data distribution and derive a more confined guarantee. Therefore, it is up to the user to determine the level of guarantee they desire after considering the effort of providing feedback.

In addition, although we assume the normal data distribution to be relatively stable, one should continuously retrain the anomaly detector with normal data to ensure it is up-to-date. Hence, it would be beneficial if there is also feedback on normal data so as to characterize the distribution. However, we do not assume to obtain them in an online manner. If the normal data distribution shifts, the update frequency should be similar to that of the anomalies. We expect a performance enhancement when feedback on normal data becomes available.

6 CONCLUSION

We have designed a general framework to guarantee accurate performance for incremental anomaly detection in IoMT. We propose to interactively incorporate the user's judgment of evolving anomaly types to construct fine-grained anomaly calibration sets, on which we compute the PAC thresholds. We provide a two-sided guarantee on FAR and MAR based on the thresholds. Besides, our framework requires limited user input (weekly labels per class). As a side benefit, the smaller calibration size reduces the computation time, allowing for faster computation. Our framework has high accuracy and provides a theoretical guarantee for detecting evolving anomalies on synthetic and VitalCore datasets. Our method can broadly apply to ensure reliability in IoT, for example, network intrusion detection systems (IDS), industrial plants, and autonomous systems. As the next step, we look forward to conducting a user study to evaluate the level of comfort among the technicians concerning the frequency of updates. Besides, we seek to provide anomaly explanations for the predicted outcomes.

The disclosure of each of the following references is incorporated herein by reference in its entirety.

REFERENCES

[1] "Medtech and the internet of medical things," https://www2.deloitte.com/uk/en/pages/life-sciences-andhealthcare/articles/medtech-and-the-internet-of-medical-things.html, accessed: June, 2021.
[2] "Projected size of the internet of things (iot) in healthcare market worldwide from 2016 to 2025," https://www.statista.com/statistics/997959/worldwide-internetofthings-in-healthcare-market-size/, published: December, 2016.
[3] R. L. Read, L. Clarke, and G. Mulligan, "Ventmon: An open source inline ventilator tester and monitor," HardwareX, vol. 9, p. e00195, 2021.
[4] H. Nguyen, R. Ivanov, S. B. DeMauro, and J. Weimer, "Repulmo: A remote pulmonary monitoring system," SIGBED Rev., vol. 16, no. 2, p. 46-50, August 2019. [Online]. Available: https://doi.org/10.1145/3357495.3357501
[5] M. Kasparick, M. Schmitz, B. Andersen, M. Rockstroh, S. Franke, S. Schlichting, F. Golatowski, and D. Timmermann, "Or. net: a service oriented architecture e for safe and dynamic medical device interoperability," Biomedical Engineering/Biomedizinische Technik, vol. 63, no. 1, pp. 11-30, 2018.

[6] B. Almadani, M. Bin-Yahya, and E. M. Shakshuki, "E-ambulance: realtime integration platform for heterogeneous medical telemetry system," Procedia Computer Science, vol. 63, pp. 400-407, 2015.

[7] M. V. Perez, K. W. Mahaffey, H. Hedlin, J. S. Rumsfeld, A. Garcia, T. Ferris, V. Balasubramanian, A. M. Russo, A. Rajmane, L. Cheung et al., "Large-scale assessment of a smartwatch to identify atrial fibrillation," New England Journal of Medicine, vol. 381, no. 20, pp. 1909-1917, 2019.

[8] A. Prudenzi, A. Fioravanti, and M. Regoli, "A low-cost internet of things integration platform for a centralized supervising system of building technology systems in hospitals," in 2018 IEEE International Conference on Environment and Electrical Engineering and 2018 IEEE Industrial and Commercial Power Systems Europe (EEEIC/I CPS Europe), 2018, pp. 1-6.

[9] D. Arney, J. Plourde, and J. M. Goldman, "Openice medical device interoperability platform overview and requirement analysis," Biomedical Engineering/Biomedizinische Technik, vol. 63, no. 1, pp. 39-47, 2018.

[10] R. Ivanov, H. Nguyen, J. Weimer, O. Sokolsky, and I. Lee, "Openicelite: Towards a connectivity platform for the internet of medical things," in 2018 IEEE 21st International Symposium on Real-Time Distributed Computing (ISORC). IEEE, 2018, pp. 103-106.

[11] J. Woodbridge, H. Noshadi, A. Nahapetian, and M. Sarrafzadeh, "Hip: Health integration platform," in 2010 8th IEEE International Conference on Pervasive Computing and Communications Workshops (PERCOM Workshops), 2010, pp. 340-345.

[12] Z. Yang, Q. Zhou, L. Lei, K. Zheng, and W. Xiang, "An iot-cloud based wearable ecg monitoring system for smart healthcare," Journal of medical systems, vol. 40, no. 12, pp. 1-11, 2016.

[13] H. Xia, I. Asif, and X. Zhao, "Cloud-ecg for real time ecg monitoring and analysis," Computer methods and programs in biomedicine, vol. 110, no. 3, pp. 253-259, 2013.

[14] Z. A. Al-Odat, S. K. Srinivasan, E. Al-qtiemat, M. A. L. Dubasi, and S. Shuja, "Iot-based secure embedded scheme for insulin pump data acquisition and monitoring," arXiv preprint arXiv: 1812.02357, 2018.

[15] P. Asare, D. Cong, S. G. Vattam, B. Kim, A. King, O. Sokolsky, I. Lee, S. Lin, and M. Mullen-Fortino, "The medical device dongle: An open-source standards-based platform for interoperable medical device connectivity," in Proceedings of the 2nd ACM SIGHIT International Health Informatics Symposium, 2012, pp. 667-672.

[16] "Neuron, medical device integration, capsule technologies," https://capsuletech.com/neuron, accessed: June, 2021.

[17] "Keras documentation: Timeseries anomaly detection using an autoencoder," https://keras.io/examples/timeseries/timeseries anomaly detection/.

[18] B. Scholkopf, R. C. Williamson, A. J. Smola, J. Shawe-Taylor, J. C. Platt et al., "Support vector method for novelty detection." in NIPS, vol. 12. Citeseer, 1999, pp. 582-588.

[19] Moloud Abdar, Farhad Pourpanah, Sadiq Hussain, Dana Rezazadegan, Li Liu, Mohammad Ghavamzadeh, Paul Fieguth, Xiaochun Cao, Abbas Khosravi, U Rajendra Acharya, et al. 2021. A review of uncertainty quantification in deep learning: Techniques, applications and challenges. Information Fusion 76 (2021), 243-297.

[20] Fadi Al-Turjman, Muhammad Hassan Nawaz, and Umit Deniz Ulusar. 2020. Intelligence in the Internet of Medical Things era: A systematic review of current and future trends. Computer Communications 150 (2020), 644-660.

[21] Parisa Alaei and Fakhroddin Noorbehbahani. 2017. Incremental anomaly-based intrusion detection system using limited labeled data. In 2017 3rd International Conference on Web Research (ICWR). IEEE, 178-184.

[22] Merve Astekin, SelimÖzcan, and Hasan Sözer. 2019. Incremental analysis of large-scale system logs for anomaly detection. In 2019 IEEE International Conference on Big Data (Big Data). IEEE, 2119-2127.

[23] Monowar H Bhuyan, Dhruba K Bhattacharyya, and Jugal K Kalita. 2012. Survey on incremental approaches for network anomaly detection. arXiv preprint arXiv: 1211.4493 (2012).

[24] Elnaz Bigdeli, Mahdi Mohammadi, Bijan Raahemi, and Stan Matwin. 2018. Incremental anomaly detection using two-layer cluster-based structure. Information Sciences 429 (2018), 315-331.

[25] Milad Chenaghlou, Masud Moshtaghi, Christopher Leckie, and Mahsa Salehi. 2018. Online clustering for evolving data streams with online anomaly detection. In Pacific-Asia Conference on Knowledge Discovery and Data Mining. Springer, 508-521.

[26] Hyonyoung Choi, Amanda Lor, Mike Megonegal, Xiayan Ji, Amanda Watson, James Weimer, and Insup Lee. 2021. VitalCore: Analytics and Support Dashboard for Medical Device Integration. In 2021 IEEE/ACM Conference on Connected Health: Applications, Systems and Engineering Technologies (CHASE). 82-86. https://doi.org/10.1109/CHASE52844.2021.00016.

[27] Raj Deshmukh and Inseok Hwang. 2019. Incremental-learning-based unsupervised anomaly detection algorithm for terminal airspace operations. Journal of Aerospace Information Systems 16, 9 (2019), 362-384.

[28] Arthur Gatouillat, Youakim Badr, Bertrand Massot, and Ervin Sejdić. 2018. Internet of medical things: A review of recent contributions dealing with cyber-physical systems in medicine. IEEE internet of things journal 5, 5 (2018), 3810-3822.

[29] Nico Görnitz, Marius Kloft, Konrad Rieck, and Ulf Brefeld. 2013. Toward supervised anomaly detection. Journal of Artificial Intelligence Research 46 (2013), 235-262.

[30] Sreelekha Guggilam, Varun Chandola, and Abani Patra. 2022. Tracking clusters and anomalies in evolving data streams. Statistical Analysis and Data Mining: The ASA Data Science Journal 15, 2 (2022), 156-178.

[31] p John C Knight. 2002. Safety critical systems: challenges and directions. In Proceedings of the 24th international conference on software engineering. 547-550.

[32] Aleksandar Lazarevic, Levent Ertoz, Vipin Kumar, Aysel Ozgur, and Jaideep Srivastava. 2003. A comparative study of anomaly detection schemes in network intrusion detection. In Proceedings of the 2003 SIAM international conference on data mining. SIAM, 25-36.

[33] Insup Lee and Oleg Sokolsky. 2010. Medical cyber physical systems. In Design automation conference. IEEE, 743-748.

[34] Shuo Li, Xiayan Ji, Edgar Dobriban, Oleg Sokolsky, and Insup Lee. 2022. PAC-Wrap: Semi-Supervised PAC Anomaly Detection. https://doi.org/10.48550/ARXIV.2205.10798.

[35] Yongxin Liu, Jian Wang, Jianqiang Li, Shuteng Niu, and Houbing Song. 2021. Class-incremental learning for wireless device identification in IoT. IEEE Internet of Things Journal 8, 23 (2021), 17227-17235.

[36] Guansong Pang, Chunhua Shen, and Anton van den Hengel. 2019. Deep anomaly detection with deviation networks. In Proceedings of the 25th ACM SIGKDD international conference on knowledge discovery & data mining. 353-362.

[37] Harris Papadopoulos, Kostas Proedrou, Volodya Vovk, and Alex Gammerman. 2002. Inductive confidence machines for regression. In European Conference on Machine Learning. Springer, 345-356.

[38] Sangdon Park, Osbert Bastani, Nikolai Matni, and Insup Lee. 2020. PAC confidence sets for deep neural networks via calibrated prediction. International Conference on Learning Representations (ICLR) (2020).

[39] Sangdon Park, Edgar Dobriban, Insup Lee, and Osbert Bastani. 2022. Pac prediction sets under covariate shift. International Conference on Learning Representations (ICLR) (2022).

[40] Adam Paszke, Sam Gross, Francisco Massa, Adam Lerer, James Bradbury, Gregory Chanan, Trevor Killeen, Zeming Lin, Natalia Gimelshein, Luca Antiga, et al. 2019. Pytorch: An imperative style, high-performance deep learning library. Advances in neural information processing systems 32 (2019).

[41] Joaquin Quiñonero-Candela, Masashi Sugiyama, Anton Schwaighofer, and Neil D Lawrence. 2008. Dataset shift in machine learning. Mit Press.

[42] Kirthanaa Raghuraman, Monisha Senthurpandian, Monisha Shanmugasundaram, V Vaidehi, et al. 2014. Online incremental learning algorithm for anomaly detection and prediction in health care. In 2014 International Conference on Recent Trends in Information Technology. IEEE, 1-6.

[43] Lukas Ruff, Robert A Vandermeulen, Nico Görnitz, Alexander Binder, Emmanuel Müller, Klaus-Robert Müller, and Marius Kloft. 2020. Deep semi-supervised anomaly detection. International Conference on Learning Representations (ICLR) (2020).

[44] Kenneth Joseph Ryan and Mark Vere Culp. 2015. On semi-supervised linear regression in covariate shift problems. The Journal of Machine Learning Research 16, 1 (2015), 3183-3217.

[45] Mahsa Salehi and Lida Rashidi. 2018. A Survey on Anomaly detection in Evolving Data: [with Application to Forest Fire Risk Prediction]. ACM SIGKDD Explorations Newsletter 20, 1 (2018), 13-23.

[46] Steffen Schneider, Evgenia Rusak, Luisa Eck, Oliver Bringmann, Wieland Brendel, and Matthias Bethge. 2020. Improving robustness against common corruptions by covariate shift adaptation. Advances in Neural Information Processing Systems 33 (2020), 11539-11551.

[47] Bernhard Schölkopf, Robert C Williamson, Alex Smola, John Shawe-Taylor, and John Platt. 1999. Support vector method for novelty detection. Advances in neural information processing systems 12 (1999).

[48] Sue Sendelbach and Marjorie Funk. 2013. Alarm fatigue: a patient safety concern. AACN advanced critical care 24, 4 (2013), 378-386.

[49] Yang Shi, Maoran Xu, Rongwen Zhao, Hao Fu, Tongshuang Wu, and Nan Cao. 2019. Interactive Context-Aware Anomaly Detection Guided by User Feedback. IEEE Transactions on Human-Machine Systems 49, 6 (2019), 550-559. https://doi.org/10.1109/THMS.2019.2925195

[50] Hongchao Song, Zhuqing Jiang, Aidong Men, and Bo Yang. 2017. A hybrid semi-supervised anomaly detection model for high-dimensional data. Computational intelligence and neuroscience 2017 (2017).

[51] Masashi Sugiyama and Motoaki Kawanabe. 2012. Machine learning in non-stationary environments: Introduction to covariate shift adaptation. MIT press.

[52] Masashi Sugiyama, Matthias Krauledat, and Klaus-Robert Müller. 2007. Covariate shift adaptation by importance weighted cross validation. Journal of Machine Learning Research 8, 5 (2007).

[53] Masashi Sugiyama, Taiji Suzuki, Shinichi Nakajima, Hisashi Kashima, Paul von Bunau, and Motoaki Kawanabe. 2008. Direct importance estimation for covariate shift adaptation. Annals of the Institute of Statistical Mathematics 60, 4 (2008), 699-746.

[54] Swee Chuan Tan, Kai Ming Ting, and Tony Fei Liu. 2011. Fast anomaly detection for streaming data. In Twenty-second international joint conference on artificial intelligence.

[55] Liang Tang, Tao Li, Florian Pinel, Larisa Shwartz, and Genady Grabarnik. 2012. Optimizing system monitoring configurations for non-actionable alerts. In 2012 IEEE Network Operations and Management Symposium. IEEE, 34-42.

[56] Vincent Vercruyssen, Wannes Meert, Gust Verbruggen, Koen Maes, Ruben Baumer, and Jesse Davis. 2018. Semi-Supervised Anomaly Detection with an Application to Water Analytics. In 2018 IEEE International Conference on Data Mining (ICDM). 527-536. https://doi.org/10.1109/ICDM.2018.00068.

[57] Pavithra Vijay. 2020. Keras documentation: Timeseries anomaly detection using an Autoencoder. https://keras.io/examples/timeseries/timeseries_anomaly_detection/.

[58] Vladimir Vovk. 2012. Conditional validity of inductive conformal predictors. In Asian conference on machine learning. PMLR, 475-490.

[59] Vladimir Vovk, Alex Gammerman, and Glenn Shafer. 2005. Algorithmic learning in a random world. Springer Science & Business Media.

[60] Markus Wurzenberger, Florian Skopik, Max Landauer, Philipp Greitbauer, Roman Fiedler, and Wolfgang Kastner. 2017. Incremental clustering for semi-supervised anomaly detection applied on log data. In Proceedings of the 12th International Conference on Availability, Reliability and Security. 1-6.

[61] Weizun Zhao, Lishuai Li, Sameer Alam, and Yanjun Wang. 2021. An incremental clustering method for anomaly detection in flight data. Transportation Research Part C: Emerging Technologies 132 (2021), 103406.

[62] Aurick Zhou and Sergey Levine. 2021. Bayesian Adaptation for Covariate Shift. Advances in Neural Information Processing Systems 34 (2021).

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system for managing a plurality of medical devices, the system comprising:

a server including at least one processor implemented in hardware;

a stream processor implemented by the at least one processor on the server for receiving medical data from a plurality of medical devices and for generating metadata and storing the medical data and the metadata for each of the devices;

data storage implemented in hardware on the server for storing the medical data and the metadata;

a communications interface implemented by the at least one processor on the server for implementing at least one communications protocol for providing access to the medical data and the metadata; and at least one application implemented by the at least one processor on the server for accessing the medical data and the metadata via the communications interface and generating, based on the medical data and the metadata, output indicative of operating status of the medical devices, wherein the at least one application includes an anomaly detector configured to monitor connection status of the medical devices, predict maintenance events concerning the medical devices as anomalies, prompt a user to confirm that the maintenance events occur as expected, and responsive to receiving user input indicating that the maintenance events occur as expected, label data corresponding to the maintenance events as expected anomalies, generate a fine-grained calibration data set including the data corresponding to the maintenance events labeled as expected anomalies and data corresponding to other connection events as unexpected anomalies, and use the fine-grained calibration data set to adaptively recalibrate the anomaly detector; and wherein the at least one application includes a ventilation alert application for extracting, in real time and from messages sent by ventilators, an expired tidal volume variable value, determining whether the expired tidal volume variable value is greater than zero, and, in response to determining that the expired tidal volume variable value is greater than zero, applying false positive detection logic that utilizes a patient name and a previous ventilator stop time to detect a false positive, and, when the false positive detection logic does not detect a false positive, sending an alert to a virtual intensive care unit.

2. The system of claim 1 wherein the medical data comprises health level seven (HL7) data.

3. The system of claim 1 the stream processor is configured to determine a device identifier and an arrival time of medical data from each of the medical devices and wherein the metadata includes a timestamp history for each of the medical devices.

4. The system of claim 3 wherein the metadata includes a latest timestamp for each of the medical devices.

5. The system of claim 1 wherein the stream processor is configured to store the medical data in a time series database.

6. The system of claim 1 wherein the communications interface is configured to provide access to the medical data via a representational state transfer (REST) or a sockets application programming interface (API).

7. The system of claim 1 wherein the at least one application comprises a medical device dashboard for graphically displaying the output indicative of the operating status of the medical devices.

8. The system of claim 7 wherein the output indicative of the operating status includes an online status and a time when a last message was received from each of the medical devices.

9. The system of claim 7 wherein the medical devices include medical devices of different types and from different medical device manufacturers.

10. The system of claim 7 wherein the output indicative of the operating status includes an indication of a time between receipt of messages from a medical device.

11. The system of claim 7 wherein the output indicative of the operating status includes an indication of a number of active medical devices connected to a server.

12. The system of claim 1 wherein the anomaly detector is configured for monitoring usage patterns of the medical devices from the medical data, for comparing the usage patterns to usage patterns reconstructed based on models, and for indicating an anomaly if a monitored usage pattern differs from any of the reconstructed usage patterns by more than a threshold amount.

13. The system of claim 12 wherein the anomaly detector is configured to generate an anomaly score for a detected instance of an anomaly, determine whether the anomaly score satisfies a probably approximately correct (PAC) guarantee based on a false alarm rate (FAR) and a miss alarm rate (MAR), and output an anomaly prediction based on the PAC guarantee.

14. A method for medical device management, the method comprising:

receiving, by a stream processor implemented on at least one processor of a server, medical data from a plurality of medical devices and generating metadata and storing, in data storage implemented in hardware on the server, the medical data and the metadata for each of the devices, wherein the at least one processor of the server is implemented in hardware;

providing a communications interface implemented by the at least one processor on the server for implementing at least one communications protocol for accessing the medical data and the metadata; and providing at least one application implemented by the at least one processor on the server for accessing the medical data and the metadata via the communications interface and generating, based on the medical data and the metadata, output indicative of operating status of the medical devices wherein the at least one application includes an anomaly detector configured to monitor connection status of the medical devices, predict maintenance events concerning the medical devices as anomalies, prompt a user to confirm that the maintenance events occur as expected, and responsive to receiving user input indicating that the maintenance events occur as expected, label data corresponding to the maintenance events as expected anomalies, generate a fine-grained calibration data set including the data corresponding to the maintenance events labeled as expected anomalies and data corresponding to other connection events as unexpected anomalies, and use the fine-grained calibration data set to adaptively recalibrate the anomaly detector;

wherein the at least one application includes a ventilation alert application, and further comprising extracting, by the ventilation alert application, in real time, and from messages sent by ventilators, an expired tidal volume variable value;

determining, by the ventilation alert application, whether the expired tidal volume variable value is greater than zero;

in response to determining that the expired tidal volume variable value is greater than zero, applying, by the ventilation alert application false positive detection logic that utilizes a patient name and a previous ventilator stop time to detect a false positive; and when the false positive detection logic does not detect a false positive, sending, by the ventilation alert application, an alert to a virtual intensive care unit.

15. The method of claim 14 wherein the medical data comprises health level seven (HL7) data.

16. The method of claim 14 wherein generating the metadata includes determining a device identifier and an arrival time of medical data from each of the medical devices and wherein the metadata includes a timestamp history for each of the medical devices.

17. The method of claim 16 wherein the metadata includes a latest timestamp for each of the medical devices.

18. The method of claim 14 comprising storing the medical data and the metadata in a time series database.

19. The method of claim 14 wherein providing the communications interface includes providing access to the medical data via a representational state transfer (REST) or a sockets application programming interface (API).

20. The method of claim 14 wherein providing the at least one application comprises providing a medical device dashboard for graphically displaying the output indicative of the operating status of the medical devices.

21. The method of claim 20 wherein the output indicative of the operating status includes an online status and a time when a last message was received from each of the medical devices.

22. The method of claim 21 wherein the medical devices include medical devices of different types and from different medical device manufacturers.

23. The method of claim 20 wherein the output indicative of the operating status includes an indication of a time between receipt of messages from a medical device.

24. The method of claim 20 wherein the output indicative of the operating status includes an indication of a number of active medical devices connected to a server.

25. The method of claim 14 wherein the anomaly detector is configured for monitoring usage patterns of the medical devices from the medical data, for comparing the usage patterns to usage patterns reconstructed based on models, and for indicating an anomaly if a monitored usage pattern differs from any of the reconstructed usage patterns by more than a threshold amount.

26. The method of claim 25 comprising generating an anomaly score for a detected instance of an anomaly, determine whether the anomaly score satisfies a probably approximately correct (PAC) guarantee based on a false alarm rate (FAR) and a miss alarm rate (MAR), and output an anomaly prediction based on the PAC guarantee.

27. A non-transitory computer readable medium having stored thereon executable instructions that when executed by at least one processor of a server control the server to perform steps comprising:

receiving, by a stream processor implemented on the at least one processor of the server, medical data from a plurality of medical devices and generating metadata and storing, in data storage implemented in hardware on the server, the medical data and the metadata for each of the devices, wherein the at least one processor of the server is implemented in hardware;

providing a communications interface implemented by the at least one processor on the server for implementing at least one communications protocol for accessing the medical data and the metadata;

providing at least one application for accessing the medical data and the metadata via the communications interface and generating, based on the medical data and the metadata, output indicative of operating status of the medical devices, wherein the at least one application includes an anomaly detector configured to monitor connection status of the medical devices, predict maintenance events concerning the medical devices as anomalies, prompt a user to confirm that the maintenance events occur as expected, and responsive to receiving user input indicating that the maintenance events occur as expected, label data corresponding to the maintenance events as expected anomalies, generate a fine-grained calibration data set including the data corresponding to the maintenance events labeled as expected anomalies and data corresponding to other connection events as unexpected anomalies, and use the fine-grained calibration data set to adaptively recalibrate the anomaly detectors wherein the at least one application includes a ventilation alert application, and the steps further include extracting, by the ventilation alert application, in real time, and from messages sent by ventilators, an expired tidal volume variable value;

determining, by the ventilation alert application, whether the expired tidal volume variable value is greater than zero;

in response to determining that the expired tidal volume variable value is greater than zero, applying, by the ventilation alert application false positive detection logic that utilizes a patient name and a previous ventilator stop time to detect a false positive; and when the false positive detection logic does not detect a false positive, sending, by the ventilation alert application, an alert to a virtual intensive care unit.

* * * * *